US006867010B1

(12) United States Patent
Pedersen et al.

(10) Patent No.: US 6,867,010 B1
(45) Date of Patent: *Mar. 15, 2005

(54) ENZYME ACTIVITY SCREEN WITH DIRECT SUBSTRATE RELOADING

(75) Inventors: Henrik Pedersen, Frodesvej 24, DK-2880 Bagsværd (DK); Swen Hölder, Frankfurt/M (DE); Jorgen Kjems, Risskov (DK); Mette Katrine Lund, Århus (DK)

(73) Assignee: Henrik Pedersen, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/390,851

(22) Filed: Sep. 7, 1999

Related U.S. Application Data

(63) Continuation of application No. PCT/DK99/00442, filed on Aug. 19, 1999.

(30) Foreign Application Priority Data

Aug. 19, 1998 (DK) .......................................... 1998 01043
Sep. 2, 1998 (DK) .......................................... 1998 01107

(51) Int. Cl.⁷ ........................ G01N 33/573; G01N 33/53
(52) U.S. Cl. ............................... 435/7.4; 435/5; 435/6; 435/7.1; 435/7.6; 435/DIG. 3; 435/DIG. 5; 435/DIG. 6
(58) Field of Search ........................... 435/7.1, 5, 6, 7.4

(56) References Cited

U.S. PATENT DOCUMENTS 5,571,681 A    11/1996 Janda
5,631,137 A  *  5/1997 Martin et al. ................ 435/7.6

FOREIGN PATENT DOCUMENTS

WO    WO 97/40141    10/1997
WO    WO 97/47314    12/1997

OTHER PUBLICATIONS

Christopher Walsh, "Enzymatic Reaction Mechanisms", 1979, W. H. Freeman and Company, 22.*
Avalle et al., (1997) Bioorganic & Medicinal Letters 7(4):479–484.
Eichler et al., (1993) Biochemistry 32:11035–11041.
Evans et al., (1996) Nature Biotechnology 14:504–507.
Dialog Information Services, Medline Accession No. 1998294385.
Dialog Information Services, Dialog Accession No. 94032215.
STN International, Caplus Accession No. 165868.
Jestin et al., Angew. Chem. Int. Ed., vol. 38, pp. 1124–1127 (1999).
Pedersen et al., Biochemistry, vol. 95, pp. 10523–10528.
Demartis et al., J. Mol. Biol., vol. 286, pp. 617–633 (1999).

* cited by examiner

Primary Examiner—Padmashri Ponnaluri
Assistant Examiner—My-Chau Tran
(74) Attorney, Agent, or Firm—Iver P. Cooper

(57) ABSTRACT

A method for in vitro selection, from a library of catalyst molecules, of a catalyst molecule of interest having a relatively more efficient specific catalytic activity of interest, as compared to the rest of the catalyst molecules within said library, and wherein said in vitro selection method is characterized by that it allows multiple catalytic activity turnovers (i.e. substrate to product catalytic activity turn-overs), by the catalyst molecule of interest, before it is finally collected. The method is based on using one or more reagent(s) which are capable of converting a product generated by a catalyst molecule of interest back into the substrate for said catalyst of interest.

Figure 1:
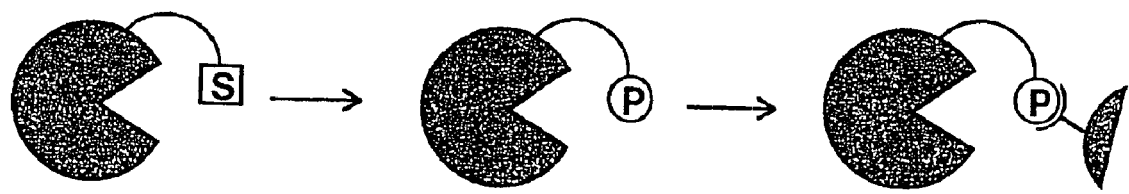

27 Claims, 14 Drawing Sheets deoxy-ribozyme (ligase)

ENZYME ACTIVITY SCREEN WITH DIRECT SUBSTRATE RELOADING

CROSS-REFERENCE TO RELATED APPLICATIONS

This application is a continuation of PCT/DK99/00442 filed Aug. 19, 1999 and claims priority under 35 U.S.C. 119 of Danish applications PA 1998 01043 filed Aug. 19, 1998 and PA 1998 01107 filed Sep. 2, 1998, the contents of which are fully incorporated herein by reference.

TECHNICAL FIELD

The present invention relates to a method for in vitro selection for a catalyst of interest, which uses multiple catalytic turnover events and direct substrate reloading.

BACKGROUND OF THE INVENTION

In the past, novel biopolymer (i.e. DNA, RNA or polypeptide) based catalysts have been created in several different ways. The following paragraphs describe some of these selection schemes.

(1). Binding to Transition State Analogs

Catalytic RNA, DNA and protein (particularly antibodies) have been isolated by this approach. It has mostly been applied to the isolation of catalytic antibodies by immunization of mice with transition state analogs (TSA), but also antibodies displayed on phage as well as RNA and DNA libraries have been challenged with TSA. The idea is that a molecule (protein, RNA or DNA) that binds a given TSA is likely to bind the substrate and stabilize the geometry and/or energetics of the transition state. This may result in catalysis.

The method does not select for catalytic activity per se, but rather for binding to a transition state analog (TSA). However, it has been included here as it is currently one of the most used methods to isolate novel catalysts. Problems encountered with this approach include: i) Detailed mechanistic knowledge of the target reaction is required (in order to design an appropriate TSA); ii) In many cases a TSA that adequately resembles the transition state is unobtainable or unstable; iii) It is not possible to mimic the structural and electronic dynamics of the reaction coordinate.

Consequently, a rather limited set of reaction types have been successfully targeted by this approach. In most cases the isolated catalysts have poor turn-over numbers.

(2). Functional Tagging of Active Catalysts

This selection scheme has been applied to protein and nucleic acids. The substrate is designed so that a reactive product is formed during the reaction (the substrate is called "suicide substrate" or "inhibitor analog"). The reactive product is likely to react with the catalyst that produced it, to form a covalent bond. As a result, active catalysts can be separated from inactive ones by way of the attached label. Catalytic antibodies displayed on phage have been isolated by this method, and it was shown in a model system that catalytically active and inactive proteins could be separated using this approach. The method should allow the isolation of rare catalysts.

Important limitations with this approach include: i) For many reactions it is not possible to design an appropriate suicide substrate. ii) Successful catalysts need only perform one turn-over during the selective process/round, which is typically on the order of minutes. Hence, there is no selective advantage for efficient catalysts.

(3). Continuous Evolution (RNA)

RNA libraries have been designed that contain both the substrate and the potentially catalytic domain in the same molecule. RNAs capable of performing the desired reaction (typically ligation) will "activate" themselves for amplification (reverse transcription followed by RNA polymerase transcription). By adequate dilutions and additions of nucleotide precursors this continuous selection can be maintained over several hours, and then analyzed.

The method has two important limitations: i) Both the substrate and the catalyst must be a nucleic acid; ii) As the catalyzed reaction and the amplification of successful enzymes is not separated, the time of the selective step is the sum of the turn-over time of the target reaction and the time of amplification of the "activated" molecules. Thus, as the amplification is on the order of seconds, there is no selective advantage for an efficient catalysts.

4. Substrate-Enzyme-Linked Selection (SELS).

Recently, methods have been described, involving the attachment of the substrate of the target reaction to a protein with potential catalytic activity towards the attached substrate (Pedersen et al., Proc. Natl. Acad. Sci., US, 1998, vol. 95, pp. 10523–10528; Jestin et al., 1999, Angew. Chem. Int. Ed., vol. 38, pp. 1124–1127; Demartis et al., 1999, JMB, vol. 286, pp. 617–633; Neri et al., 1997, WO 97/40141). Upon intramolecular conversion of the substrate, the active catalyst can be isolated by means of the attached product.

This scheme is very general. However, as successful catalysts need only perform one turn-over during the selective process/round, which is typically on the order of minutes, there is no selective advantage for efficient catalysts. For the same reason, it presumably is not possible to distinguish enzymes with slightly different specific activity with this selection scheme.

SUMMARY OF THE INVENTION

The problem to be solved by the present invention is to provide a method for in vitro selection, from a library of catalyst molecules, of a catalyst molecule of interest having a relatively more efficient specific catalytic activity of interest, as compared to the rest of the catalyst molecules within said library, and wherein said in vitro selection method is characterised by that it allows multiple catalytic activity turn-overs (i.e. substrate to product catalytic activity turn-overs), by the catalyst molecule of interest, before it is finally collected.

The solution is based on using a sample comprising a number of individual units in said in vitro selection method and further wherein said selection method is characterised by the use of one or more reagent(s) which are capable of converting a product generated by a catalyst molecule of interest back into the substrate for said catalyst of interest. See FIG. 1 for a graphic illustration of an individual unit.

Accordingly, in a first aspect the invention relates to a method for in vitro selection, from a library of catalyst molecules, of a catalyst molecule of interest having a relatively more efficient specific catalytic activity of interest as compared to the rest of the catalyst molecules within said library and wherein said in vitro selection method is characterised by that it allows multiple catalytic activity turn-overs (i.e. substrate to product catalytic activity turn-overs by the catalyst molecule of interest, before it is finally collected and wherein said method comprises following steps, (i) placing; a sample comprising a number of individual units wherein said sample comprises a library of catalyst molecules provided in the form of individual units, wherein the individual units comprise a first type individual unit having the following general structure:

C-S, wherein C denotes a catalyst molecule and S a substrate which is capable of being catalysed into a product by at least one catalyst comprised within said library of catalyst molecules and thereby providing the possibility of obtaining a second type individual unit comprising the general structure:

C-P, wherein C has the meaning defined above and P is the product molecule resulting from the catalytic conversion of the substrate S of the first type individual unit; and (a) the substrate S is attached to the catalyst in a configuration that allows catalytic reaction between the catalyst and the substrate within said individual unit; and (b) the nature of said attachment of the substrate and the catalyst provides the possibility, by means of a characteristic of the product, of isolating an entity comprising information allowing the unambiguous identification of the catalyst molecule which has been capable of catalysing the reaction substrate molecule to product molecule;

under suitable conditions where a catalyst molecule of interest performs its catalytic activity of interest and where said method is characterised by that said sample is further under conditions wherein the product generated by a catalyst of interest are in contact with one or more reagent(s) which convert it back into the substrate S;

(ii) selecting for a catalyst of interest by selecting for one or more individual unit(s) which comprise(s) the product molecule; and (iii) isolating an entity comprising information allowing the unambiguous identification of the catalyst molecule of interest which has been capable of catalysing multiple times the reaction substrate to product, by means of a characteristic of the product; and optionally (iv) repeating step (i) to (iii) one or more times by using the information comprised in said entity of step (iii) to generate the catalyst molecule of interest and construct an individual unit comprising said generated catalyst molecule of interest and then using this individual unit as a starting material in said repetition step.

The term "said sample is further under conditions wherein the product generated by a catalyst of interest is in contact with one or more reagent(s) which convert it back into the substrate", according to step (i) of the first aspect of the invention, denotes any reagent(s) and any combination of reagent(s) molecules which can catalyse the reaction product (comprised within the individual unit) ($P_1$) to the substrate (comprised within the individual unit) ($S_1$) or that participates as a reactant in the reaction $P_1$ to $S_1$. For further description of this and description of preferred embodiment of said reagent(s) reference is made to the section "Guidance to a skilled person when searching for a suitable reagent" below. Further, see FIG. 2 for a graphic illustration.

The term "an individual unit", comprised within a sample according to first aspect as described above, denotes an individual unit comprising the general structure as specified under point (i) in the first aspect of the invention and a substrate molecule attached to a catalyst molecule as specified under point (a) and (b) in the first aspect of the invention. See FIG. 1 for a suitable example of such an individual unit.

The term "an individual unit comprising the general structure: a catalyst-a substrate; or a catalyst-a product" denotes that said individual unit comprises at least one molecule of each of said identities, i.e. at least one catalyst molecule and at least one substrate molecule or at least one product molecule. Accordingly, said individual unit may for instance comprise more than one copy of an identical catalyst molecule or may comprise several different catalyst molecules.

Further the term "-" placed between the individual identities within said individual unit denotes that there is a physical connection between said individual identities within said individual unit, i.e. that there is a physical connection between a catalyst-a substrate or a catalyst-a product.

Further, "an individual unit" as described herein denotes an individual unit wherein it is possible to physically separate said individual unit from the other different individual units, within said sample, in order to be able to isolate the separate individual unit.

The term "different individual units" denotes different individual units each independently comprising different catalyst molecules, i.e. an example of two different individual units may be (1) catalyst molecule$^1$-substrate; and (2) catalyst molecule$^2$-substrate;

wherein catalyst molecule$^1$ and catalyst molecule$^2$ denotes two different catalyst molecules.

The term "a sample comprising a number of different individual units" denotes a sample comprising at least two different individual units, preferably at least 100 different individual units, more preferably at least 10.000 different individual units, more preferably at least $10^6$ different individual units, even more preferably at least $10^8$ different individual units, and most preferably at least $10^{14}$ different individual units. Basically the actual number of different individual units corresponds to the actual size of the library of catalyst molecules.

The term "a sample comprising a number of individual units" and the term "a sample comprising a number of different individual units" may be used interchangeably herein.

The term "a library of catalyst molecules" denotes a library comprising at least two different catalyst molecules, preferably at least 100 different catalyst molecules, more preferably at least 10.000 different catalyst molecules, more preferably at least $10^6$ different catalyst molecules, even more preferably at least $10^8$ different catalyst molecules, and most preferably at least $10^{14}$ different catalyst molecules.

The term "a substrate capable of being catalysed into a product molecule by at least one catalyst molecule comprised within said library of catalyst molecules" basically denotes any suitable substrate molecule. Essentially said substrate molecule is chosen according to the specific catalytic activity which it is desired to select for. For instance, if the desired catalytic activity is a protease activity then a suitable substrate may be a peptide molecule and the product will then be a degraded peptide. The terms "substrate" and "substrate molecule" may be used interchangeably.

The term "product" denotes the product obtained by the catalytic reaction substrate to product by a catalyst of interest as specified herein. The terms "product" and "product molecule" may be used interchangeably.

The term "catalyst" denotes any catalyst molecule with a desired catalytic activity, such as organic and inorganic molecules, proteins, enzymes, peptides, nucleic acids, biopolymers and non-biological polymers, small organic or inorganic molecules. The terms "catalyst" and "catalyst molecule" may be used interchangeably.

The term "the substrate is attached to the catalyst in a configuration that allows catalytic reaction between the catalyst and the substrate within said individual unit" denotes a direct or indirect physical connection, within each of the individual units, between substrate and catalyst. This connection should preferably maximize productive interaction of the catalyst and the substrate, within the individual unit, while minimizing the interaction of catalysts and substrates on different individual units.

The term "the nature of said attachment of the substrate and the catalyst provides the possibility, by means of a characteristic of the product, of isolating an entity comprising information allowing the unambiguous identification of the catalyst molecule which has been capable of catalysing multiple times the reaction substrate molecule to product molecule" according to point (b) of the first aspect of the invention denotes that said entity is isolated by means of one or more characteristic of the product.

An example of a suitable characteristic of the product may be that said product does not bind to a matrix and the substrate does bind to a matrix. In this case a suitable selection protocol may be that the individual units are bound to the solid support on the form a catalyst-a substrate-matrix, and released when it is on the form catalyst-a product. For a detailed description of an example of such a system reference is made to a working example herein (vide infra).

Another example of a suitable characteristic of the product may be that said product is binding to a receptor as illustrated in FIG. 1.

The term "an entity comprising information allowing the unambiguous identification of the catalyst which has been capable of catalysing multiple times the reaction substrate molecule to product molecule" according to point (b) in the first aspect of the invention, denotes either an entity wherein said information is carried in the catalyst molecule as such or an entity comprising other kind of information providing the possibility of unambiguously identifying the catalyst. Such other kind information may for instance be an entity comprising a DNA sequence encoding a peptide or a polypeptide when the catalyst molecule of interest is a peptide or a polypeptide. An illustration of this may be when the isolated entity is a filamentous phage comprising a DNA sequence encoding a polypeptide of interest attached on the surface of said phage. See e.g. FIG. 5 and below for further details.

The term "under suitable conditions where a catalyst molecule of interest performs its catalytic activity of interest" according to step (i) of the first aspect of the invention, denotes any suitable conditions where a catalyst molecule of interest performs its catalytic activity of interest.

Such suitable conditions may be alkaline pH if the purpose of the selection is to identify a catalyst of interest having activity at alkaline pH.

The term "the catalyst molecule of interest which has been capable of catalysing multiple times the reaction substrate to product" according to step (iii) of the first aspect of the invention denotes that said catalyst molecule of interest has performed the catalytic reaction substrate to product at least two times, more preferably at least 100 times, more preferably at least 10.000 times, more preferably at least $10^6$ times, and most preferably at least $10^{10}$ times.

The term "repeating step (i) to (iii) one or more times by using the information comprised in said entity of step (iii) to generate the catalyst molecule of interest and construct an individual unit comprising said generated catalyst molecule of interest and then using this individual unit as a starting material in said repetition step" according to point (iv) in first aspect of the invention denotes that said repetition may be one time, more preferably 2 times, more preferably more than 5 times, even more preferably more than 10 times, and most preferably more than 25 times.

Figure 2:
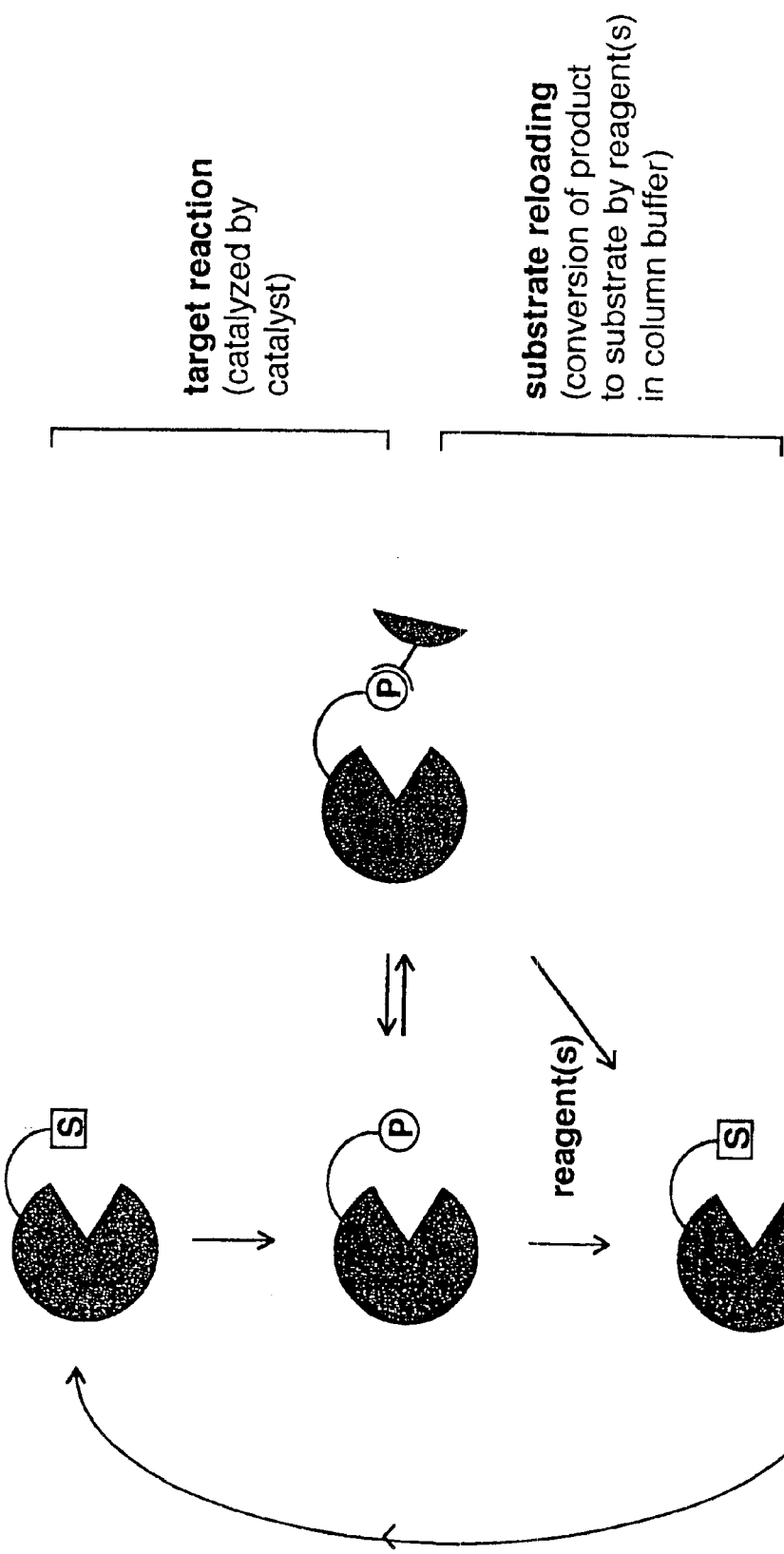

An advantage of the method for in vitro selection as described above is that it allows the catalyst molecules to perform multiple turn-overs of substrate to product during one selection round (i.e. before the catalyst molecules(s) of interest is finally collected) (see FIG. 2 for an illustration).

This is fundamentally different from previous in the art described selection protocols, which either involved binding to a transition state analog of the target reaction, wherein there is no turn-over of substrate (see #1 in "Background" above) or a single turn-over rate (#2, 3 and 4 in "Background" above).

This may provide two advantages, which may be illustrated by the following possible selection scheme using the method of the invention (see FIG. 2 for an illustration):

a) placing, according to point (i) of the first aspect of the invention, the sample comprising a number of individual units under suitable conditions where a catalyst molecule of interest exhibits its catalytic activity of interest and further under conditions wherein said individual units are in contact with a reagent molecule(S) at one end (starting end) of a product-binding column wherein a receptor specifically binding the product is coupled to the matrix of the product-binding column and with a suitable amount of the reagent(s) within the product-column buffer;

b) selecting, according to point (ii) of the first aspect of the invention, for a catalyst molecule of interest by selecting for one or more individual unit(s) which comprise (s) the product molecule, by collecting the individual unit(s) which arrive(s) latest to the opposite end (collecting end) of the column.

Within this selection scheme the following events, among others, take place within the product-column:

1) individual units comprising a potential catalyst molecule of interests convert the attached substrate to the product reaction;

2) said individual units, now comprising the product, are diffusing to and binding to a receptor placed close to the starting end of the product column;

3) the reagent molecules, within the product-column buffer mediates the reaction product to substrate and thereby generating the unit structure catalyst molecule-linker-substrate, and thereby said released individual units above are now comprising a substrate and a potential catalyst molecule of interests, which has made one catalytic conversion of the substrate to product, and is now regenerated in the original form of the individual units of point 1. Accordingly, said units can therefore once more perform reaction (1); binding to a receptor relatively closer to the collecting end of the product column etc.

The catalyst molecule of interest having most efficient specific catalytic activity of interest will perform most substrate to product conversions in a given time interval, and as a result, will spend more time immobilised on the product-binding receptor. Therefore, the individual unit(s)

comprising said most efficient catalyst molecule will arrive latest to the collecting end of said column.

Using this example of a method of the second aspect of the invention, two advantages over the art may be:

i) that the possible "selectable" catalytic activity may be much higher than for the prior art selection protocols. A selective step involves performing the target reaction, diffusion to and binding of product to product-binding column, and finally the regeneration of attached substrate from attached product by the reagent (s). Since diffusion is generally a fast process, the selection stringency can be controlled simply by the amount of product binding receptor on the column or the type/amount of Y-S component in the product-column buffer;

ii) minor differences in activity can be distinguished; Since the selective step is reiterated many times as the catalysts flow through the column, even minor differences in catalyst activity will result in differential retention on the column, and thus differential enrichments.

Accordingly, an advantage over the art my be that minor differences in activity can be distinguished; since the selective step is reiterated many times during the selection scheme and even minor differences in catalyst activity may then be differentiated.

In another aspect the invention relates to a method for producing a catalyst molecule of interest comprising performing the method for multiple catalytic activity turn-over in vitro selection according to the invention and the further following step, (a) producing said isolated catalyst molecule of interest in a suitable quantity of interest by a suitable production method.

DRAWINGS

FIG. 1: Graphic illustration of a suitable example of a first type individual unit having the following general structure:

C-S, wherein C denotes a catalyst molecule and S a substrate. The substrate S is attached to the catalyst in a configuration that allows catalytic reaction between the catalyst and the substrate within said individual unit. The catalytic reaction results in a second type individual unit:

C-P, wherein C denotes a catalyst molecule and P denotes a product molecule.

The nature of said attachment of the substrate and the catalyst provides the possibility, by means of a characteristic of the product (e.g. binding affinity to a matrix), of isolating an entity (e.g. the catalyst itself or a phage displaying it) comprising information allowing the unambiguous identification of the catalyst molecule which has been capable of catalysing the reaction from substrate molecule to product molecule.

FIG. 2: A graphic illustration of a suitable example wherein a sample of the invention is under conditions wherein the product generated by a catalyst of interest are in contact with one or more reagent(s) which actively convert it back into the substrate. This allows multiple catalytic activity turn-overs (i.e. substrate to product catalytic activity turn-overs), by the catalyst molecule of interest, before it is finally collected.

Figure 3:
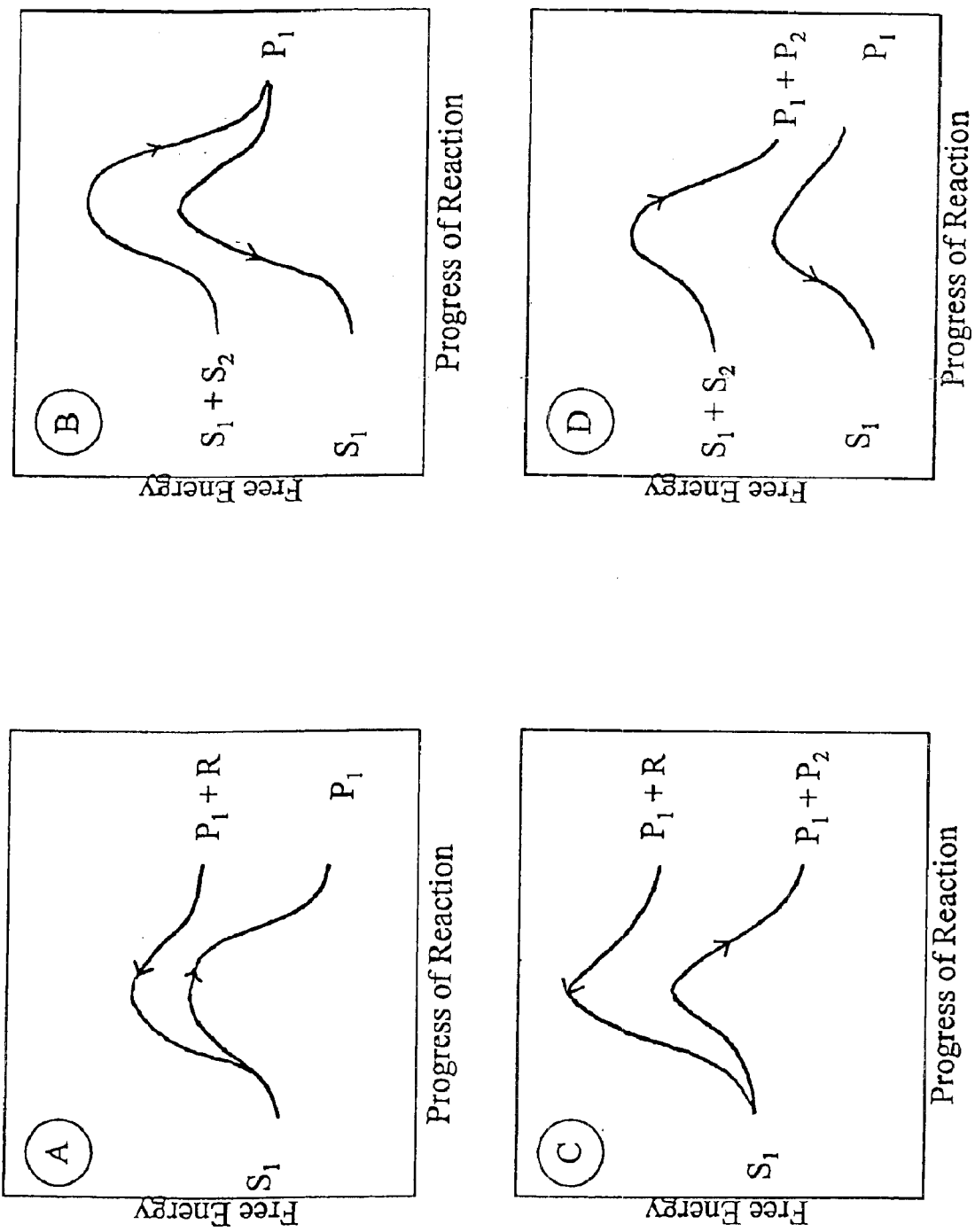

FIG. 3: A figure showing preferred requirements for a reagent capable of converting the product back to the substrate as described herein.

Definitions:

S1: Substrate attached to individual unit prior to target reaction.

P1: Product attached to individual unit after target reaction has occurred.

S2: All additional substrates of forward (target) reaction.

P2: Represents all additional products of forward reaction.

R: Reactants of the reverse reaction (reactants are thus reagents).

Figure 4:
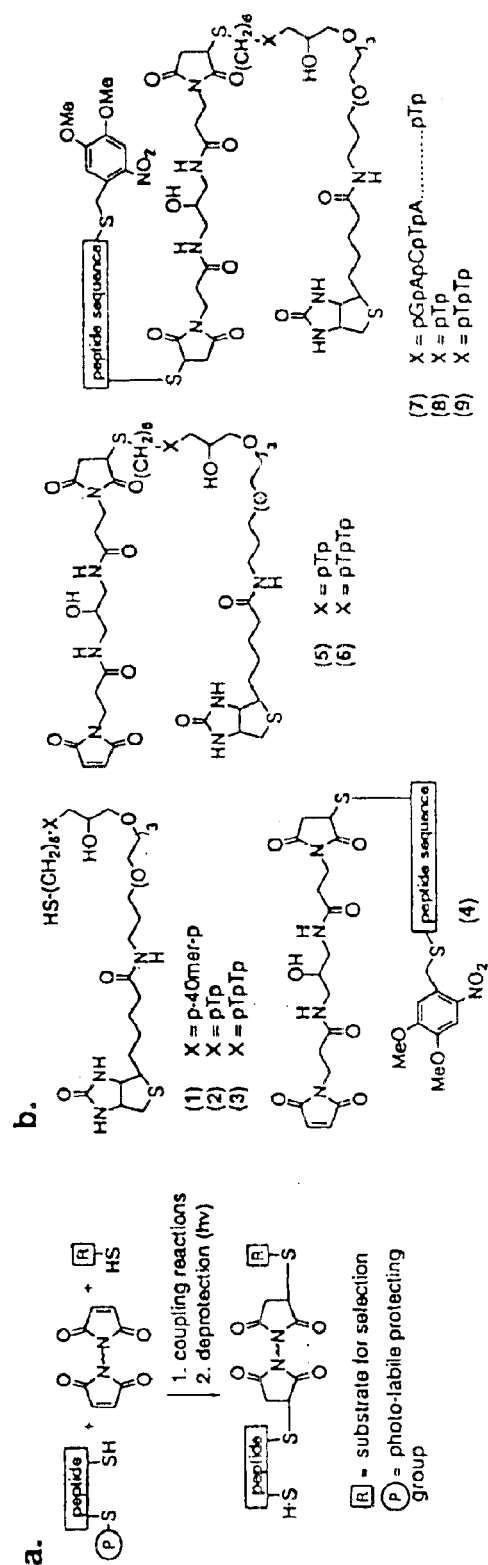

FIG. 4: Structures and synthesis of base-linker-substrate conjugates.

Figure 5:
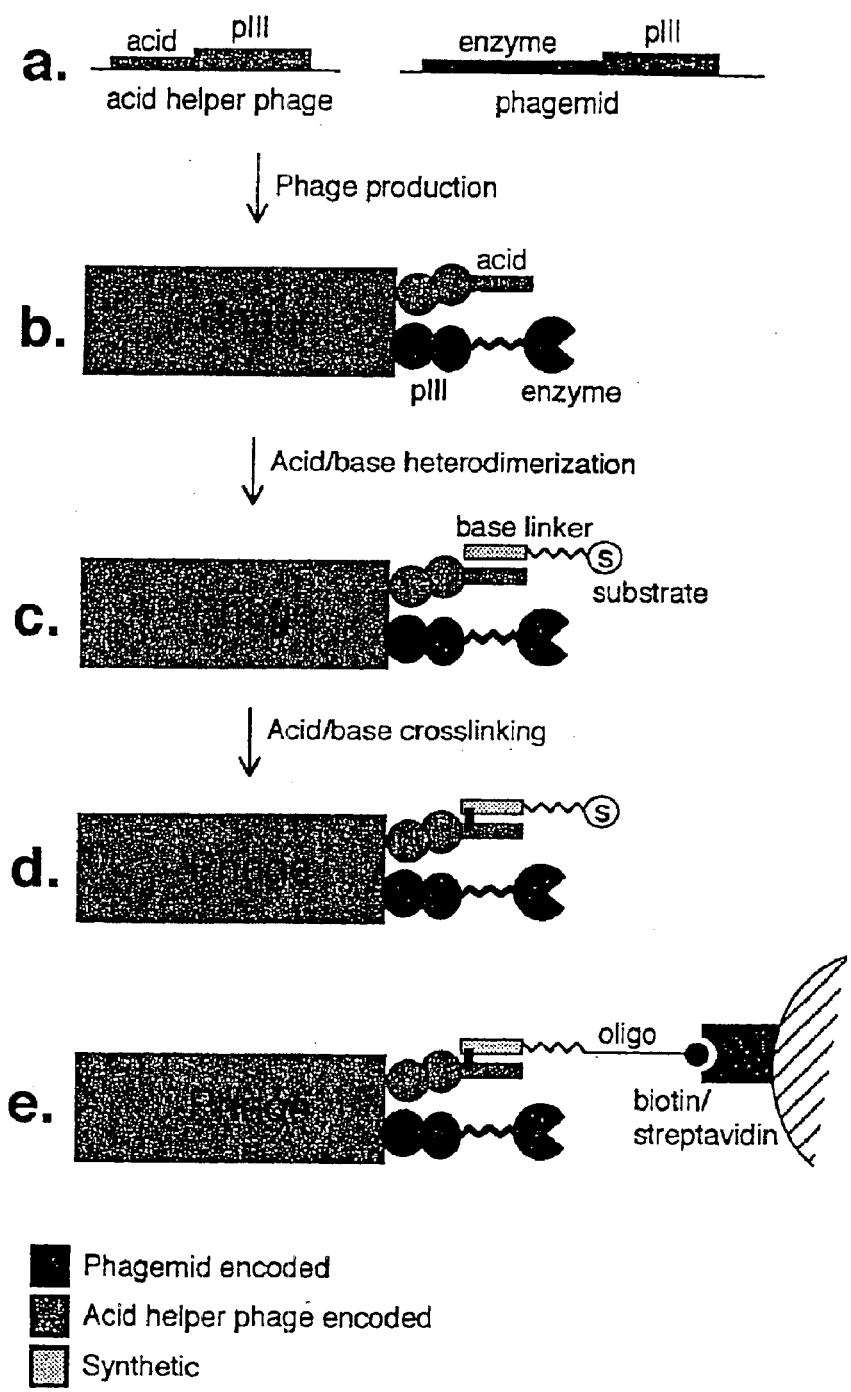

FIG. 5: Covalent attachment of substrate to the pIII protein on phage. (a) DNA encoding the acid peptide sequence and a C-terminal cysteine was fused to the N-terminal end of gene gIII, to form the acid helper phage. A phagemid encodes the protein library in fusion with the pIII protein; (b) Phage production leads to phage particles displaying the phagemid encoded protein; the pIII proteins have acid peptide extensions; (c) Coiled-coil formation of the acid and base peptides noncovalently attaches the substrate to the phage pIII protein; (d) Removal of the reducing agent leads to crosslinking of acid and base peptides through their C-terminal cysteines; (e) In the present study phages displaying staphylococcal nuclease are attached to streptavidin beads through a 5'-biotinylated, single-stranded oligodeoxynucleotide. Phages displaying active enzyme are released by cleavage of the oligodeoxynucleotide in an intramolecular reaction.

Figure 6:
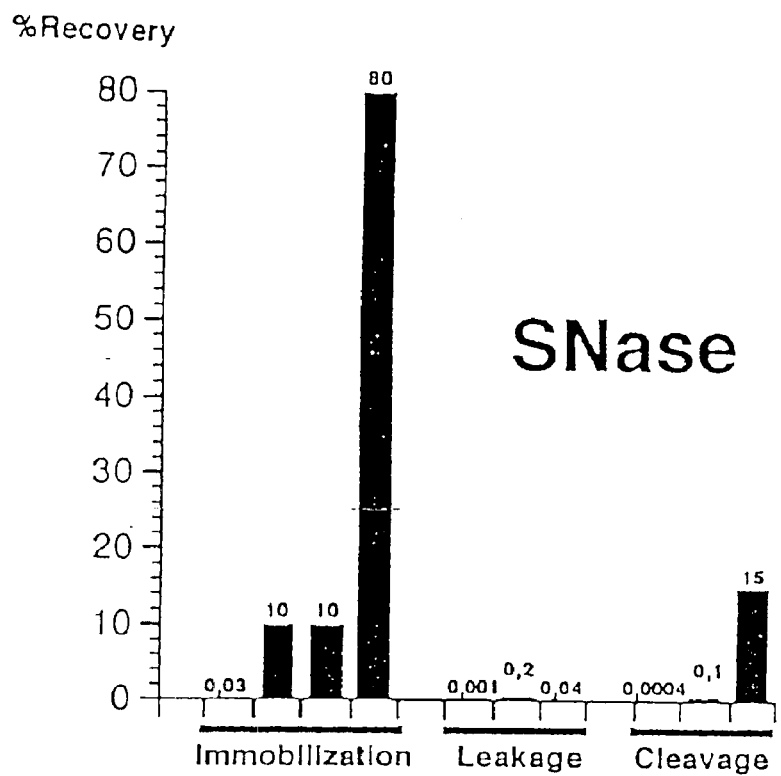
Figure 6:
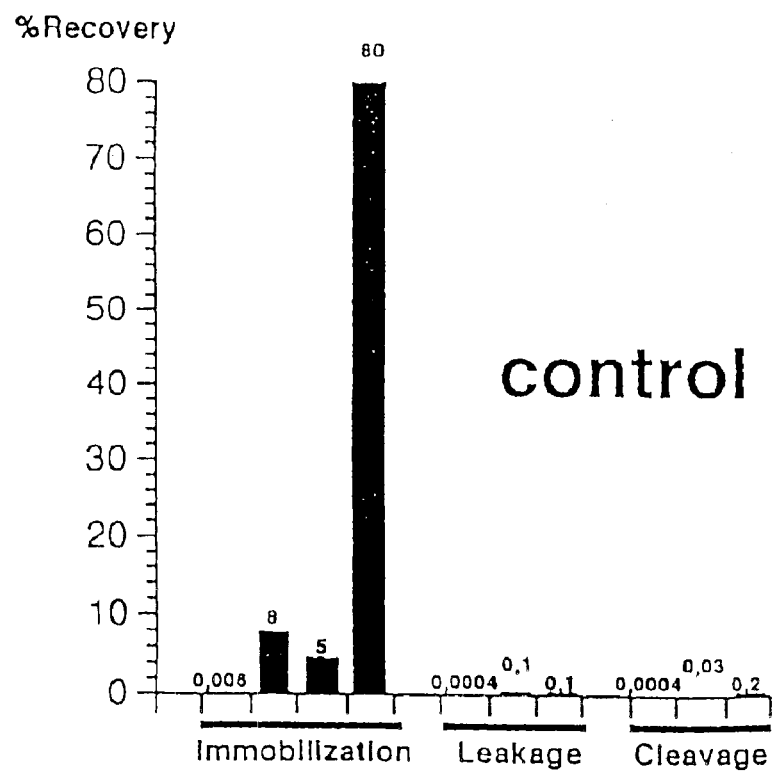

FIG. 6: Immobilization and cleavage of phage from solid support. Either no base-linker, the base-linker-pTp or the base linker-oligodeoxynucleotide conjugate was crosslinked to (a) phage displaying SNase or (b) the control protein Fab 39-A11. Columns 1–4 show immobilization on streptavidin beads. Immobilization was either examined by phage titering of the beads directly (columns 1–3), or after DNase I treatment of the beads (column 4); columns 5–7 show leakage (release in absence of $Ca^{2+}$); columns 8–10 shows $Ca^{2+}$ induced release (cleavage). The percent recovery is shown in parantheses above the columns.

Figure 7:
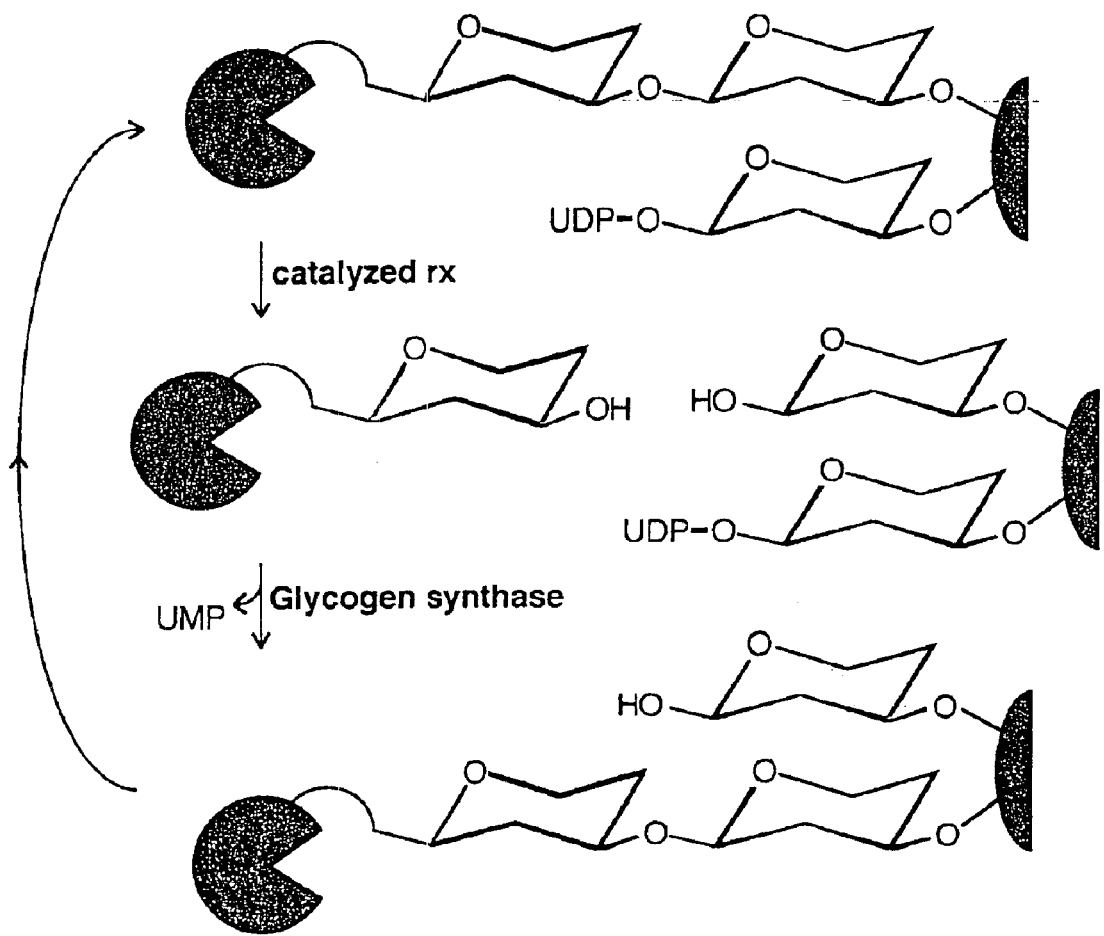

FIG. 7: A figure supporting the description in working example 2 herein (vide infra). Optimization of an enzyme with glycosidase activity.

Figure 8:
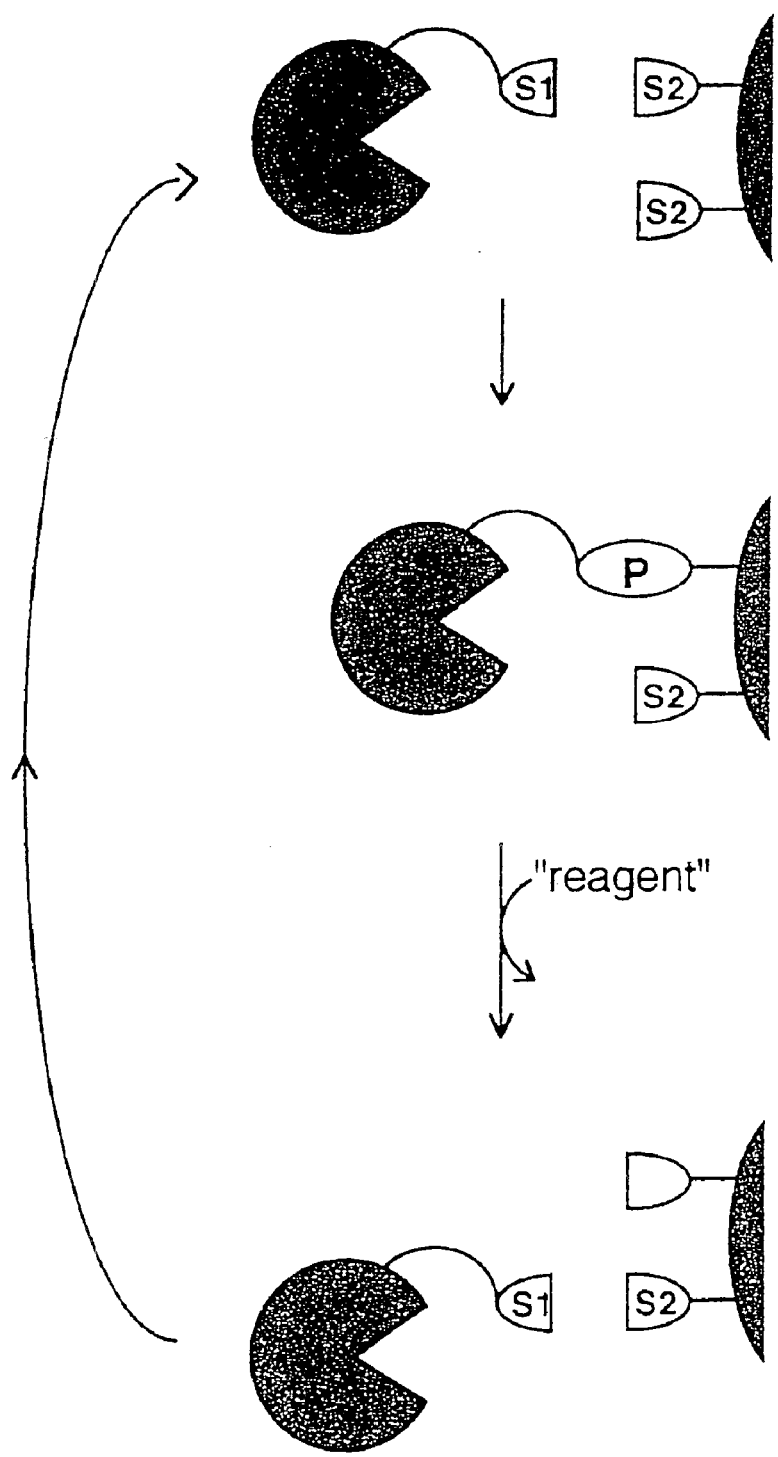

FIG. 8: Graphic illustration of a method for in vitro selection, wherein the selecting for a catalyst molecule of interest, is done by specific immobilization to the product molecule. This may be done by a reverse method, wherein substantially each of the individual units comprising the substrate molecule and the catalytic molecule is bound to a matrix, and wherein the unit is released from said matrix when the substrate is converted into the product.

Figure 9:
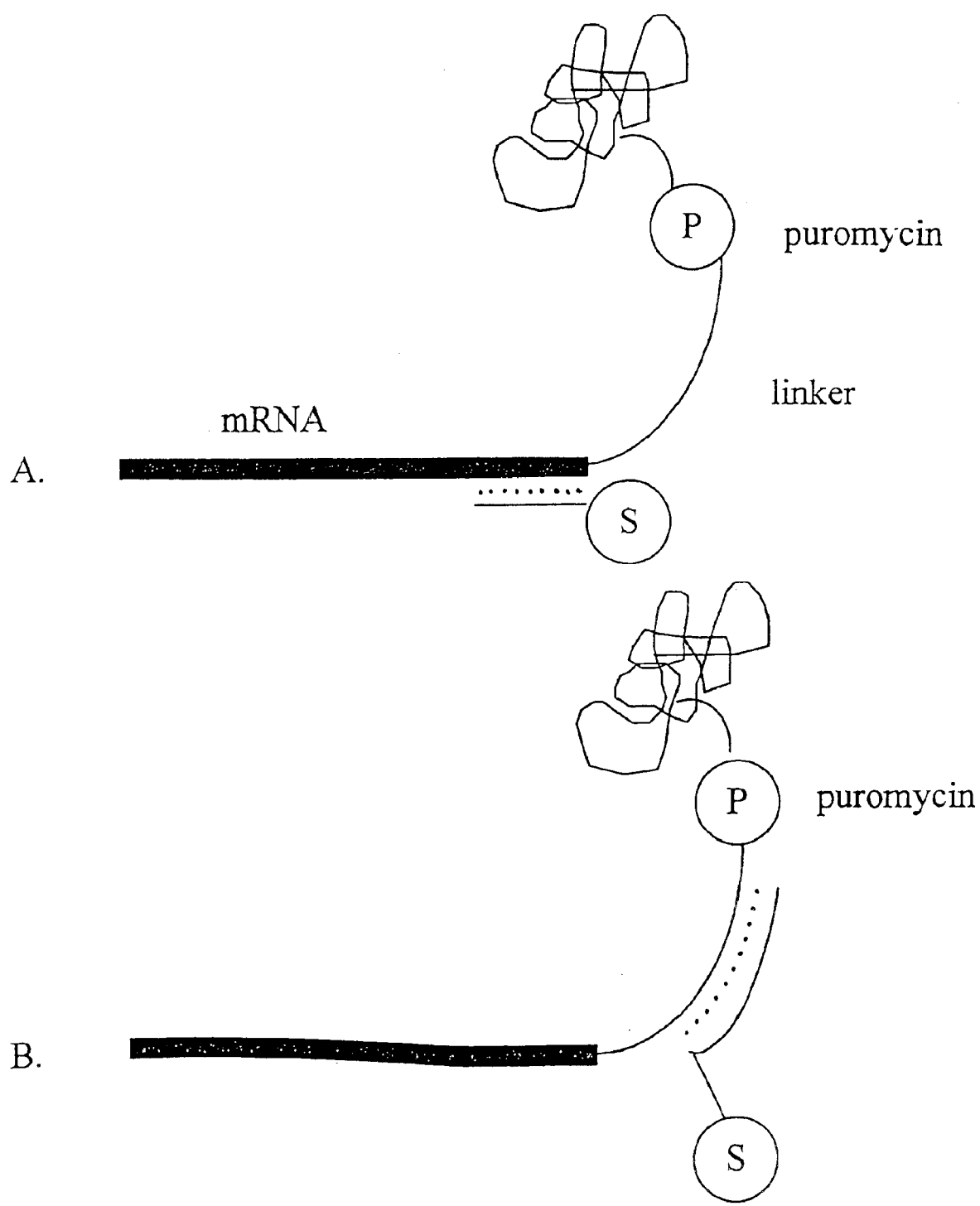

FIG. 9: A figure supporting the description in working example 3 herein (vide infra). An example of an individual unit comprising the features of the first aspect of the invention.

Figure 10:
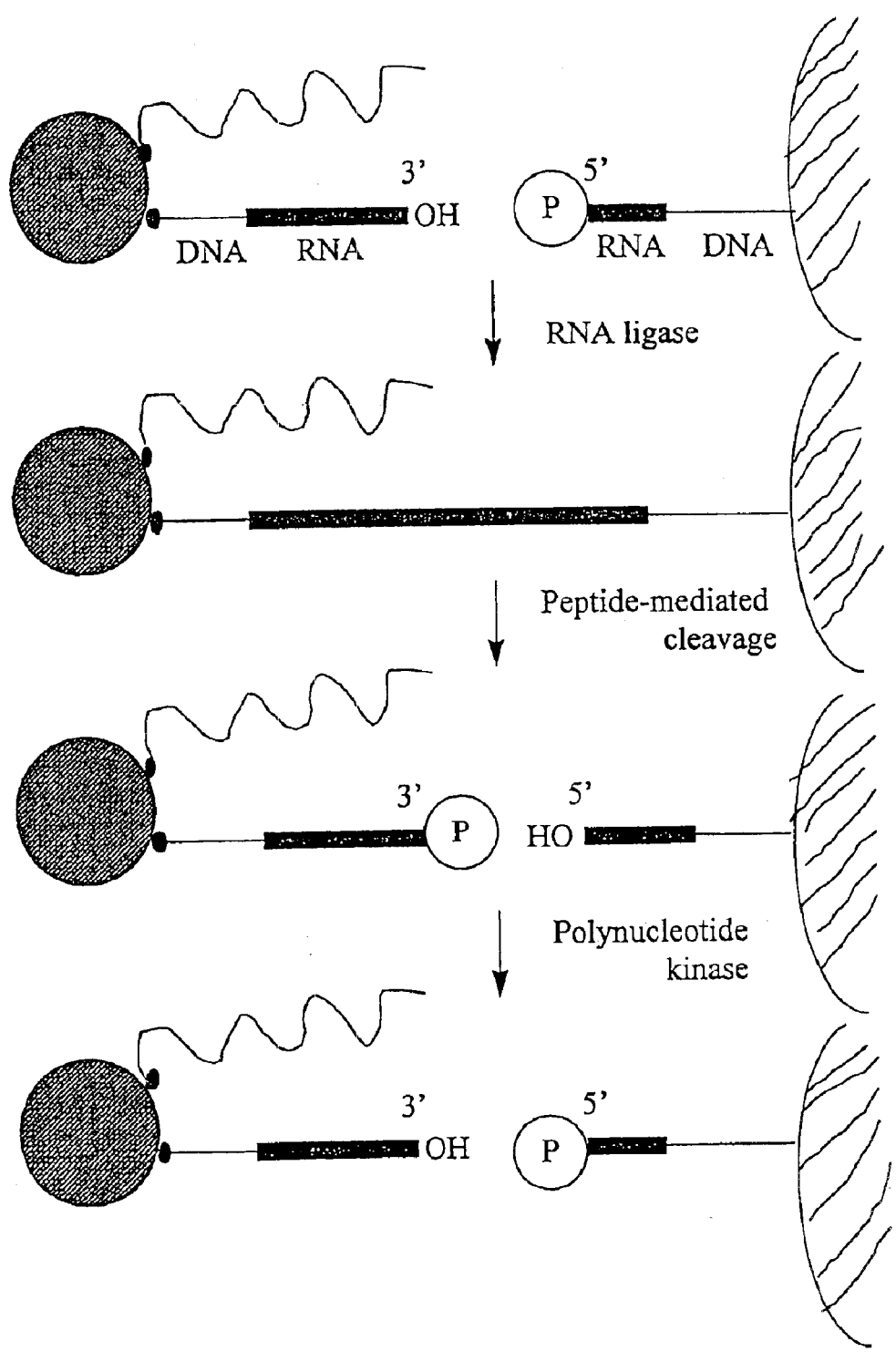

FIG. 10: A figure supporting the description in working example 5 herein (vide infra). Enrichment of wildtype RNase A peptide on beads.

Figure 11:
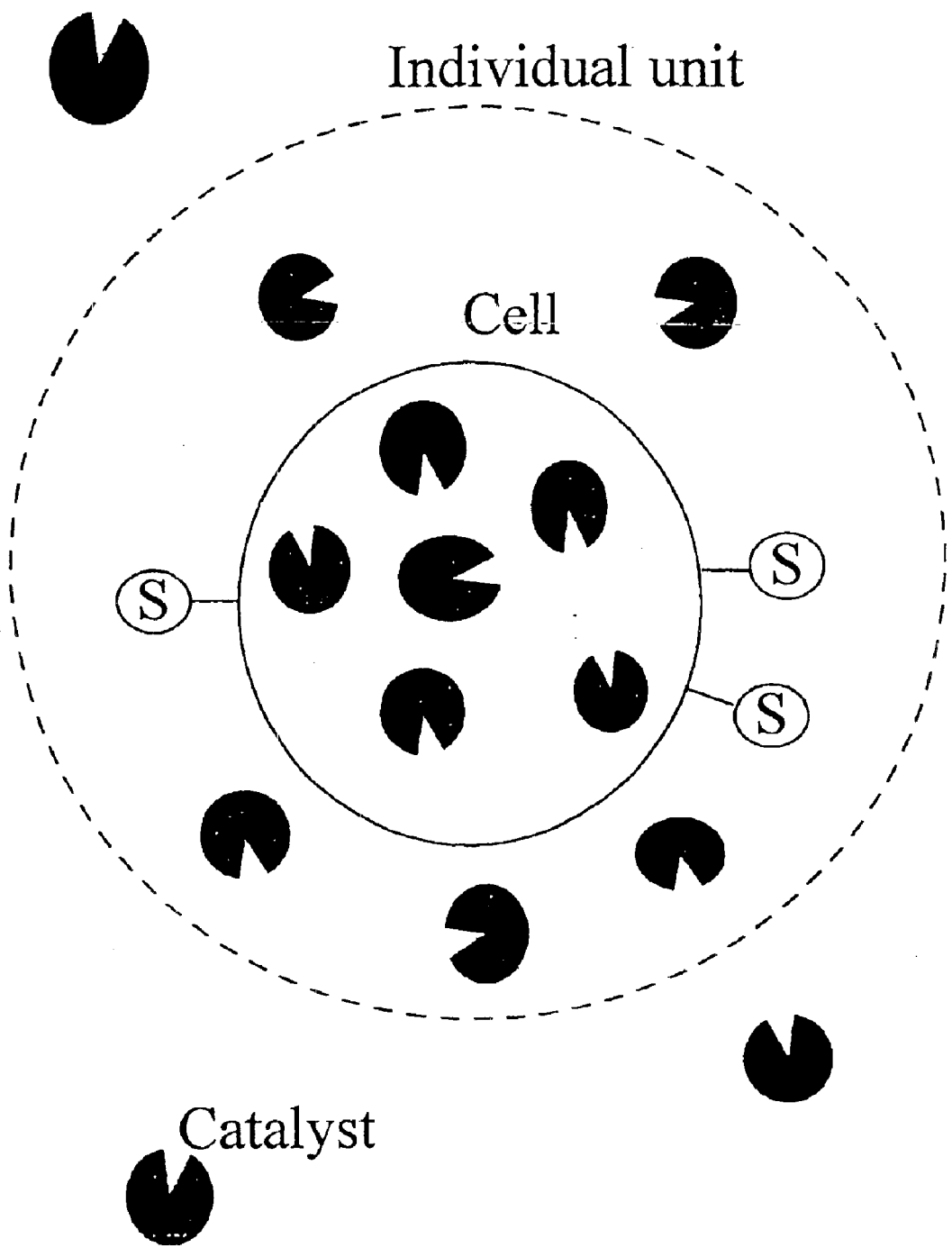

FIG. 11: A figure supporting the description in working example 4 herein (vide infra). Optimization of a secreted enzyme's activity.

Figure 12:
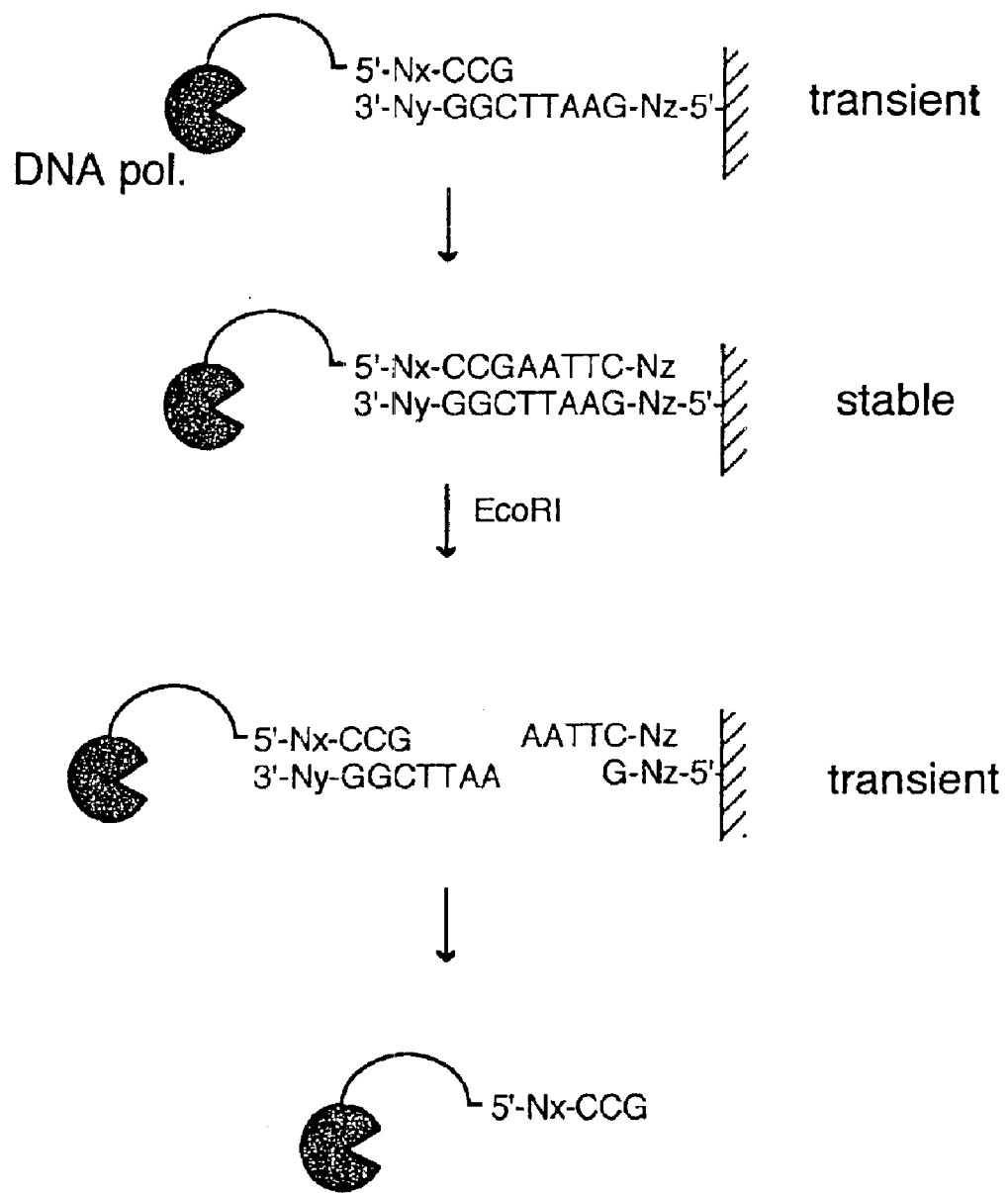

FIG. 12: A figure supporting the description in working example 6 herein (vide infra). Isolation of active DNA polymerase variants displayed on phage.

Figure 13:
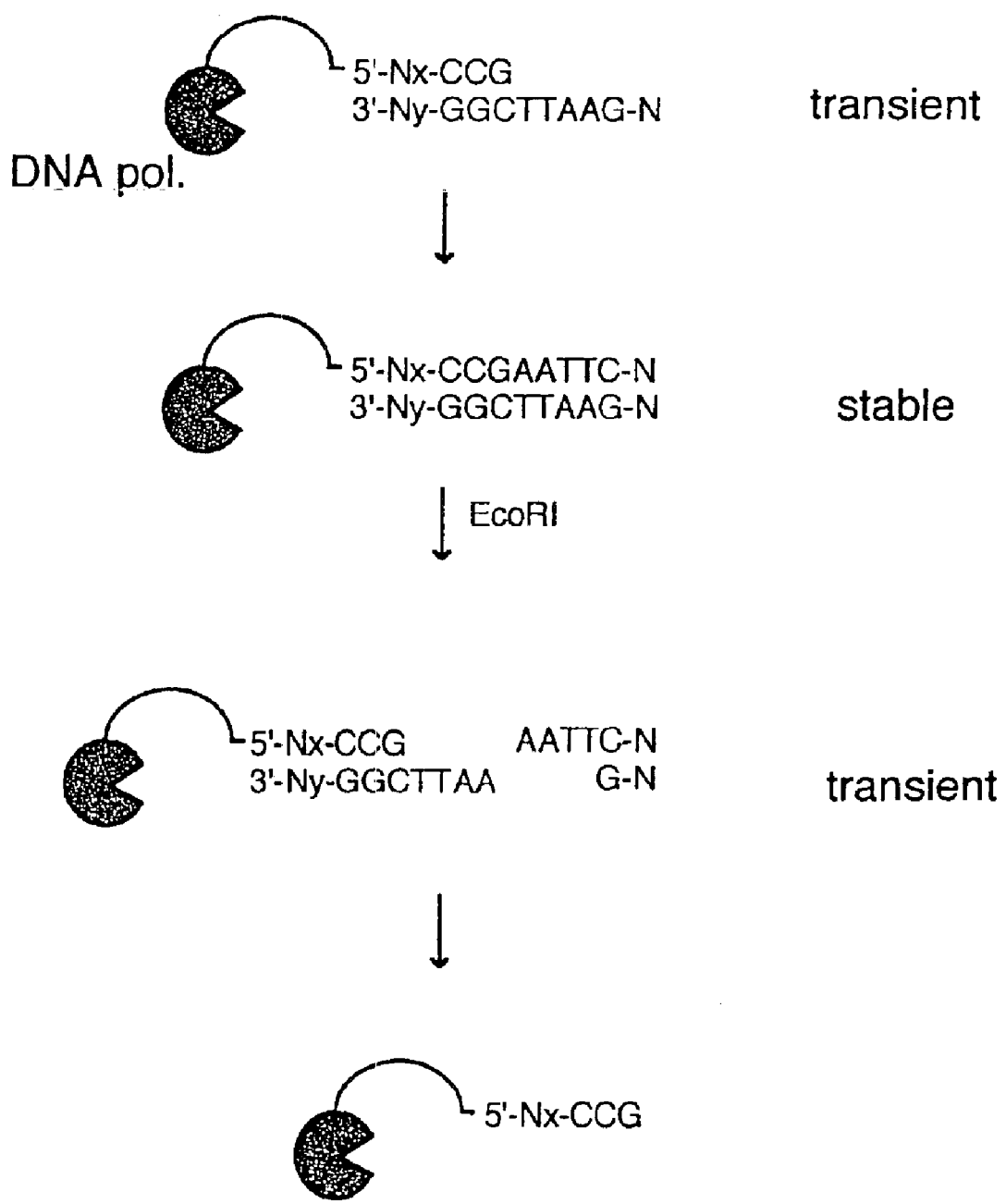

FIG. 13: A figure supporting the description in working example 7 herein (vide infra). Isolation of DNA polymerase variants by electrophoresis.

Figure 14:
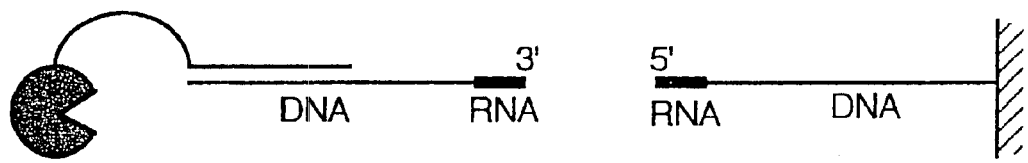

FIG. 14: A figure supporting the description in working example 8 herein (vide infra). Optimization of a deoxyribozyme with ligase activity.

Embodiment(s) of the present invention is described below, by way of examples only.

DETAILED DESCRIPTION OF THE INVENTION

A Method for Multiple Catalytic Activity Turn-Over In Vitro Selection, According to the First Aspect of the Invention:

The term "selection" preferably denotes that the selection according to step (ii) in the first aspect of the invention, is performed on more than one, preferably more than 1000, more preferably more than $10^6$, even more preferably more than $10^{10}$ and most preferably more than $10^{14}$ individual units comprised within a sample, preferably without interference of the skilled person.

The term "Column" denotes herein all kinds of solid support. Examples are: columns, surfaces including biacore apparatus. Further In some cases there is no need for a solid support. This is the case if the separation is based on migration in an electric field.

The Product Generated by a Catalyst of Interest are in Contact with One or More Reagent(s) which Convert it Back into the Substrate:

As described above, the term "said sample is further under conditions wherein the product generated by a catalyst of interest are in contact with one or more reagent(s) which convert it back into the substrate", according to step (i) of the first aspect of the invention, denotes any reagent(s) and any combination of reagent(s) molecules which can catalyses the reaction product (comprised within the individual unit) ($P_1$) to the substrate (comprised within the individual unit) ($S_1$) or that participates as a reactant in the reaction $P_1$ to $S_1$. For further description of this and description of preferred embodiment of said reagent(s) reference is made to the section "Guidance to a skilled person when searching for a suitable reagent" below. Further, see FIG. 2 and FIG. 3 for a graphic illustration.

During selection rounds performed according to the method for multiple catalytic activity turn-over in vitro selection, according to the invention, it may be advantageous to perform the first selection rounds less stringently than later selection rounds. This can for example be done by employing a low concentrations of reagent(s) in the column buffer, and/or by using lower amounts of product binding receptor immobilized on the column matrix. In certain cases it may be desirable in the first round(s) to use no Y-substrate. Also, less efficient reagent(s) or product binding receptors can be used. In later selection rounds the concentrations are then increased. To further increase the stringency of the selections, one may add excess substrate S to the buffer to serve as a competitor substrate. Other ways to modify selection stringency include variation of the length of the linker that connects enzyme and substrate, addition of factors to the column buffer with affinity for the substrate or enzyme, or addition of factors that affects substrate-enzyme interaction (eg. receptors/antibodies binding the enzyme's active site, enzyme inhibitors, receptors/antibodies with affinity for the substrate).

Finally, in order to limit the time available to the catalysts for substrate turn-over, pulses of for example electricity or light may be applied during the selection. Appropriately separated pulses could create for example transient pH- or ionic gradients that would initiate the reaction substrate to product, performed by the catalyst. The pulses should be separated enough in time that it allows plenty of time for a catalyst in solution to become immobilized on a receptor before the pulse initiates the next reaction. In this way, the dead time of the selection performed in the column format (i.e. the time the catalyst spends diffusing from one receptor to the next) can be drastically reduced, and very high stringencies obtained.

Generally speaking, it is within the skilled persons general knowledge to optimize the specific experimental set-up.

For illustration, as a non-limiting example, it is preferably in cases where the reagent(s) cannot efficiently act on the immobilized product, but only on the free product, the affinity of the column for the product must be adjusted to establish an appropriate equilibrium between the unbound and bound product. However, the optimal selection stringency is obtained if the reagent(s) act on both free product and product immobilized on column.

Examples of suitable "reagent(s) are given below:
"Desired reaction", "Reagent(s)":
1. "DNA polymerization", "DNase"
2. "RNA polymerization", "RNase"
3. "RNA polymerization using nucleotides containing unnatural bases", "RNA backbone cleaving enzyme"
4. "Glycogen degradation", "UDP-glucose+glycogen synthase"
5. "Polysaccharide synthesis", "Polysaccharide cleaving enzyme"
6. "Sequence specific dsDNA cleavage", "Sequenase+deoxy-ribonucleoside-triphosphates"
7. "Ester hydrolysis", "activated nucleophile"
8. "Amid bond formation", "protease"
9. "Lipid hydrolysis", "acetylCoA+"lipid synthase"
10. "phosphorylation", "phosphatase"
11. "Ester hydrolysis", "1-(3-dimethylaminopropyl)-3-ethylcarbodiimide hydrochloride (EDC)+alcohol"
12. "D-to-L form isomerization", "L-to-D isomerase"
13. "Proline trans-to-cis isomerization", "Proline cis-to-trans isomerase"
14. "Lactone or lactam cyclization", "Lactonase or Lactamase"
15. "Oxidation or reduction", "Reductase or Oxidase"
16. "Desulfotation", "Sulfotransferase"

Guidance to a Skilled Person when Searching for a Suitable Reagent:

The conversion product to substrate molecule is in this paragraph termed "direct reloading" or "substrate reloading".

"Conditions" are in this paragraph defined in the context of the direct reloading protocol set-up, i.e., under conditions where substrate $S_1$ and product $P_1$ are attached to the individual unit comprising the catalyst as described above. Further see FIG. 3 for an illustration of this $S_1$, $P_1$, $S_2$, $P_2$ definition.

A catalyst cannot alter the equilibrium of a chemical reaction. In other words, a catalyst accelerates the forward and reverse reaction by the same factor. However, under conditions where the reactants have not yet reached equilibrium, a catalyst can accelerate the attainment of equilibria.

In order for the direct substrate reloading protocol to work optimally, the reaction catalyzed by the "catalyst" (individual unit) preferably is energetically favorable, i.e., the catalyzed (target) reaction is energetically downhill under the conditions of the assay (see FIG. 3, A-D). The following examples describe some of the many possible combinations of "target reactions" and "reagent(s)" that might be feasible with the direct reloading protocol. The characteristics of reagent(s) that work is described in each case, in order to guide the skilled person to the right choice of reagent(s).

FIG. 3A depicts a reaction involving only one substrate ($S_1$) and one product ($P_1$), both attached to the "catalyst". An example of one such reaction could be the isomerization of a compound ($S_1$) to its isomer ($P_1$). The conversion of $S_1$ to $P_1$ is energetically downhill, and is a reaction that can be targeted with the protocol proposed. The reverse reaction, conversion of $P_1$ to $S_1$ would be energetically uphill; therefore, the buffer should contain a reactant that, together with $P_1$, is at a higher energy than $S_1$. An example of one such reactant is ATP; in the example, the buffer would contain both ATP and an enzyme that could use the energy stored in ATP to isomerize $P_1$ to $S_1$ (ATP would not necessarily react with, $P_1$, but rather, the enzyme would couple the energetically unfavourable conversion of $P_1$ to $S_1$ with the energetically favourable hydrolysis of ATP).

FIG. 3B shows a forward reaction involving more than one substrate but only one product. An example would be RNA polymerization, in which the S1 substrate is the 3'-hydroxyl group on a ribonucleotide, and the S2 substrates are various ribonucleoside-triphosphates in solution. The forward reaction would be driven by hydrolysis of the ribonucleoside-triphosphates, and therefore be energetically downhill. However, the substrate reloading process (regeneration of the 3'-hydroxyl) would also be downhill. At a first glance this may seem odd; however, the two processes proceed along different reaction pathways (for example, the ribonucleoside-triphophates are not regenerated). In principle, the reverse reaction does not require an enzyme. However, in the example the reverse process is a hydrolysis of a phosphodiester bond, which is a very slow process. Substrate reloading would therefore be much more efficient if a ribonuclease was added.

FIG. 3C involves one substrate S1 and two or more products P1 and P2, of lower energy than S1. Reactant is added to the buffer; the reaction of reactant with P1 to form S1 is energetically downhill, as it must be for the set-up to work. This set-up could be used for "catalysts" (individual units) that catalyzed the hydrolysis of glycogen (i.e., the S1 substrate would be glycogen), and therefore the P1 product attached to the catalyst would be a (polymer of) glucose. The reagents could include the enzyme glycogen synthase, which generates glycogen from UDP-glucose and the (polymer of) glucose. The enzyme thus couples the energetically favourable hydrolysis of UDP-glucose with the energetically unfavourable fusion of glucose units.

FIG. 3D describes a more complex situation, in which more than one substrates is transformed into more than one products. Again, the formation of products is down the energy hill; FIG. 3D describes a situation where formation of S1 from P1 is spontaneous (does not require a reactant). If the target reaction is an ATP-dependent isomerization (thus, S2=ATP and P2=ADP), and S1 and P1 are isomers, then the isomerization of P1 to S1 might be energetically downhill (and not require any additional reactant). The efficiency of the substrate reloading process could be speeded up by addition of another catalyst (enzyme) catalyzing the ATP-independent isomerization.

It is important to remember that water molecules could be regarded as substrates in for example hydrolysis reactions.

Also, despite what is said above, the direct reloading selection can be set up in a way so that the target reaction is not thermodynamically downhill under the conditions of the assay. Consider for example a target reaction where S1 is cleaved to form P1 and P2, and an excess of P2 is present in the buffer so that formation of S1 from P1 and P2 is energetically favoured, i.e., the equilibrium is towards formation of S1. However, since the equilibrium is dynamic, S1 will continuously be degraded and formed, but at any time there will be more S1 than P1. When the individual event S1 to P1 and P2 occurs, the P1 may be isolated (eg., bound to a product-binding column), and therefore, the catalyst will be isolated with it. The excess P2 will result in a very efficient substrate reloading, but will not exclude the forward reaction from occuring.

Preferably, the reagent(s) should regenerate the substrate S1 attached to the catalyst.

Preferably, the reagent(s) regenerate the substrate by a reaction pathway different from the pathway that generated the product.

A Sample Comprising a Number of Different Individual Units:

As specified above said sample may comprise at least two different individual units and up to numerous different individual units.

The actual number of different individual units generally corresponds to the actual size of the library of catalyst molecules.

Beside said specified different individual units said sample may in principle also comprise any other suitable material.

Further said different individual units comprised within said sample may be dissolved in any suitable buffer, such as water.

Different Individual Units:

As described above an individual unit comprises the general structure:

a catalyst-a substrate; or if the substrate has been converted into the product the general structure:

a catalyst-a product.

Further, the term "different individual units" denotes different individual units each independently comprising different catalyst molecules, i.e. an example of two different individual units may be (1) catalyst molecule$^1$-substrate; and
(2) catalyst molecule$^2$-substrate;

wherein catalyst molecule$^1$ and catalyst molecule$^2$ denotes two different catalyst molecules.

Further, "an individual unit" as described herein denotes an individual unit wherein it is possible to physically separate said individual unit from the other different individual units, within said sample, in order to be able to isolate the separate individual unit.

A Biologically Amplifiable Individual Unit:

An embodiment of the invention relates to a sample comprising a number of different individual units according to the invention, wherein said individual units of point (i) according to the first aspect of the invention is a biologically amplifiable individual unit.

Another embodiment of the invention relates to a sample comprising a number of different individual units according to the invention, wherein said individual units of point (i) according to the first aspect of the invention is a biologically amplifiable individual unit and both said substrate and said catalyst molecule are attached on the surface of said biologically amplifiable individual unit.

The term "a biologically amplifiable individual unit" denotes that within said individual unit either;

(i) the catalyst molecule of interest is a biologically amplifiable molecule; or
(ii) the catalyst molecule of interest is biologically encoded by the information comprised within the entity allowing the unambiguous identification of the catalyst molecule;

providing the possibility of amplifying said catalyst molecule of interest in order to obtain multiple copies of said catalyst molecule.

The term "biologically encoded" in point (ii) above denotes that the information is comprised within a DNA or RNA molecule in the form of the genetic codons.

An example of a biologically amplifiable individual unit in relation to point (i) above is an individual unit wherein the catalyst molecule of interest is a DNA or a RNA molecule, since it is well known in the art that DNA or RNA molecules may easily be amplified.

An example of an biologically amplifiable individual unit in relation to point (ii) above is an individual unit wherein the catalyst molecule of interest is a peptide or polypeptide and wherein said entity comprising information allowing the unambiguous identification of the catalyst molecule is a DNA molecule encoding said peptide or polypeptide.

In relation to the second example above, a physical connection must exist between the peptide and the DNA that encodes it, in order to isolate the DNA with the peptide it encodes. The connection can be either direct, in which case the peptide is attached directly to the nucleic acid that encodes it, or indirect, in which the peptide is attached to the surface of for example a cell that contains the nucleic acid encoding it, or alternatively, is secreted from the cell and therefore the concentration is higher around the substrate attached to the same cell than it is at the substrates attached to the other cells of the sample. Such a cell is herein termed a "carrier system" as will be further discussed below.

Flexible Linker:

An embodiment of the invention relates to a sample comprising a number of different individual units according to the first aspect of the invention, wherein said individual unit of point (i) comprises following structure: catalyst molecule-flexible linker-substrate.

The term "flexible linker" refers herein to the molecules as a whole connecting the catalyst with substrate. For example, if the substrate is attached to a bead through a flexible molecule, and the catalyst is also attached to the bead through a flexible molecule, "flexible linker" will refer to "flexible molecule-bead-flexible molecule", and the characteristics of the flexible linker will reflect the individual characteristics of the two flexible molecules and the portion of the bead that connects the two. Flexible linkers may for instance consist of flexible polypeptides, polyethylen glycol (PEG), and other polymers of reasonable flexibility.

Further, a flexible linker may also connects the catalyst molecule and a carrier system (see below).

Carrier Systems

An embodiment of the invention relates to a sample comprising a number of different individual units according to the invention, wherein said individual unit of point (i) in the first aspect of the invention comprises the following structure: catalyst molecule-carrier system-substrate, or more preferably the structure: catalyst molecule-carrier system-flexible linker-substrate.

The term "carrier system" denotes a system/entity which physically connects the catalyst molecule and the substrate, or alternatively, carries the information allowing the unambiguous identification of the catalyst molecule, and wherein said carrier system does not directly participate in the catalytic reaction substrate to product catalysed by the catalyst molecule.

Such a carrier system is herein further divided into a biologically amplifiable carrier system and a biologically non-amplifiable carrier system.

Examples of biologically amplifiable carrier systems include (carrier system-catalyst molecule): phage-polypeptide (Boublik et al., 1995, Biotechnol (NY), vol. 13, pp. 1079–1084), filamentous phage-peptide (Kay, Winter and McCafferty, 1996, "Phage Display of Peptides and Proteins, A Laboratory Manual", Academic Press), retrovirus-polypeptide (Buchholz et al., 1998, Nature Biotechnology, vol. 16, pp. 951–954), plasmid-peptide (Schatz et al., 1996, Meth. Enzym., vol. 267, pp. 171–191), polysome-peptide (Mattheakis et al., 1994, Proc. Natl. Acad. Sci. USA, vol. 91, pp. 9022–9026; He and Taussig, 1997, Nucleic Acids Research, vol. 25, pp. 5132–5134), bacteria-peptide (Brown, 1997, Nature Biotechnology, vol. 15, pp. 269–272) and mRNA-peptide (Roberts and Szostak, 1997, Proc. Natl. Acad. Sci. USA, vol. 94, pp. 12297–12302), cDNA-peptide (analogous to the mRNA-protein fusion display, except that the protein has been attached to a cDNA of the mRNA that encodes it, rather than to the mRNA itself), peptide-secreting cell-peptide (Kinsella and Cantwell, 1991, Yeast, vol. 7, pp.445–454), peptide-secreting artificial microsphere peptide (artificial microspheres containing proteins expressed from the genes contained within the microsphere, see Tawfik and Griffiths, 1998, Nature Biotechnology, vol. 16, pp. 652–656).

Examples of biologically non-amplifiable carrier systems include (carrier system-catalyst molecule): bead-organic molecule or bead-peptide (Brenner and Lerner, 1992, Proc. Natl. Acad. Sci. USA, vol. 89, pp. 5381–5383).

It should be noted that an individual unit comprising the beads-DNA sequence structure is herein a biologically amplifiable unit (se above), however the carrier system, as such (bead) is a biologically non-amplifiable carrier system.

Catalyst and Library of Catalyst Molecules:

As stated above the term "catalyst" denotes any catalyst molecule with a desired catalytic activity, such as organic and inorganic molecules, proteins, peptides, nucleic acids, biopolymers and non-biological polymers, small organic or inorganic molecules. Further the terms "catalyst" and "catalyst molecule" may be used interchangeably.

Accordingly, a further embodiment of the invention relates to, (i) a method according to the invention, wherein said library of catalyst molecules is a library of natural or unnatural peptides or polypeptides, preferably a library of enzymes; or (ii) a method according to the embodiment (i) immediately above, wherein said library is a library comprising a number of different enzymatic activities; or (iii) a method according to the embodiment (i) above, wherein said library comprises variants derived from one or more precursor polypeptide(s), wherein said precursor polypeptide(s) exhibit(s) closely related enzymatic activities.

The term "library comprising a number of different enzymatic activities" preferably denotes a library wherein said different enzymatic activities are substantially different activities, e.g. protease, amylase activities. An advantage of such an library may be that it is possible to change the substrate according to the specific activity of interest. If for instance a protease of interest first is isolated by a method for in vitro selection as described herein by use of e.g. a peptide as substrate, then an amylase may be isolated thereafter by chancing the substrate to e.g. a starch molecule.

Said libraries may be made according to any of the numerous standard known processes of making such libraries.

Accordingly, a further embodiment of the invention relates to a sample comprising a number of different individual units according to the embodiments of invention mentioned immediately above, wherein said library is a library comprising shuffled/recombined/doped polypeptides.

The term "natural or unnatural peptides or polypeptides" denotes that the peptides or polypeptides be a kind found in Nature, or of a kind that is artificially produced by Man. Another embodiment of the invention relates to, (i) a method according to the invention, wherein said library of catalyst molecules is a library of natural or unnatural nucleic acids;

(ii) a method according to the embodiment (i) immediately above, wherein said library is a library comprising nucleic acids having a number of different catalytic activities; or (iii) a method according to the embodiment (i) above, wherein said library is a library comprising nucleic acid variants derived from one or more precursor nucleic acid(s), wherein said precursor nucleic acid(s) exhibit(s) closely related catalytic activities.

The term "library comprising nucleic acids having a number of different catalytic activities" preferably denotes a library wherein said different catalytic activities are substantially different activities, e.g. nuclease, ligase, isomerase, phosphorylase. An advantage of such a library may be that by changing the substrate according to the specific activity of interest, said library may be used to identify a number of nucleic acids of interest. If for instance a DNA ligase of interest first is isolated by a method for in vitro selection as described herein by use of, e.g., two DNA oligonucleotides as substrates, then a ribonuclease may be isolated thereafter by changing the substrate to, e.g., an RNA oligonucleotide.

Said libraries may be made according to any of the numerous standard known processes of making such libraries.

Accordingly, a further embodiment of the invention relates to a sample comprising a number of different individual units according to the embodiments of invention mentioned immediately above, wherein said library of nucleic acids is a library comprising shuffled/recombined/doped nucleic acids.

The term "natural or unnatural nucleic acids" denotes that the nucleic acids may contain any of the five natural bases (A, T, G, C, U), or any unnatural base or backbone structure.

Further embodiments of the invention relates to (i) a sample comprising a number of different individual units according to the invention, wherein said library of catalyst molecules is a library comprising natural polymer molecules, or unnatural polymer molecules, or small organic molecules, or small inorganic molecules or a mixture of said molecules; or (ii) a sample comprising a number of different individual units according to the embodiment mentioned immediately above, wherein said library is made by combinatorial chemistry.

Preferably, the sample may contain a virtual combinatorial library (Proc. Natl. Acad. Sci. USA, 1997, vol. 94, pp. 2106–2110), in the sense that each potential catalyst is made up of more than one subunit, held together by reversible covalent or non-covalent interactions, and the subunits associate and dissociate several times during the multiple turn-over assay.

In the context of virtual combinatorial libraries, the term "unambiguous identification" which is used throughout this text, should be understood in terms of the unambiguous identification of the recovered entities, but not necessarily the composition of entities of the individual catalyst. Such catalysts, isolated from virtual combinatorial libraries, could be catalysts made up of several polypeptide chains, held together by weak interactions (as for example protein subunit association, characterized by low subunit—subunit affinities), or held together by reversible covalent disulfide-bonds, whose exchange rates have been accelerated by the addition of redox-buffers (eg. oxidized and reduced glutathione) and therefore continuously are associating and dissociating.

Alternatively, the library members could be assemblies of small organic molecules held together by disulfide bonds.

In an even further embodiment the invention relates to a sample comprising a number of individual units according to the invention, wherein the catalyst molecules and the substrate capable of being catalysed into a product (point (i) in the first aspect) are of a different chemical substance.

The term "catalyst molecules and the substrate capable of being catalysed into a product (point (i) in the first aspect) are of a different chemical substance" denotes that said catalyst molecule and the substrate molecule are of a substantially different chemical substrate.

The term "natural polymer molecules, or unnatural polymer molecules" denotes that the polymers may be of a kind found in Nature, or of a kind that is artificially produced by Man.

Performing an Enrichment Step Prior to Step (i) of the Second Aspect of the Invention Certain proteins are difficult to display on filamentous phage. In particular large proteins or proteins which have a toxic or growth inhibiting effect on *E. coli* often have low display efficiency, i.e. the majority of phage particles produced carry no displayed proteins on the surface. Display efficiencies as low as one out of a thousand phages displaying the protein of interest have been reported (Jestin et al., 1999, Angew. Chemi. Int. Ed., vol. 38, pp. 1124–1127; Demartis et al., 1999, JMB, vol. 286, pp. 617–633). In such cases, a high non-specific background is expected, because of the large excess of phage particles carrying the DNA encoding the protein of interest, but not displaying said protein on the surface. To circumvent this potential problem, an affinity tag may be coupled to the C-terminal end of the protein of interest, allowing the purification of phages displaying full-length tagged protein column chromatography.

A non-limiting variety of affinity tags that may be used in this manner is: histidine tag (example 9), intein-chitin binding domain fusion (Chong et al., 1997, Gene, vol. 192, pp 271–281), FLAG peptide (Slootstra et al., 1997, Molecular Diversity, vol. 2, pp. 156–164), and the maltose binding protein (Pryor and Leiting, 1997, Protein expression and Purification, vol. 10, pp. 309–319).

Accordingly, embodiments of the invention relate to (i) a method for in vitro selection according to the first aspect of the invention, wherein the catalyst molecules of interest are enzymes or proteins that have been coupled to an affinity tag, and wherein an optional step is performed prior to step (i), the optional step comprising an enrichment for individual units displaying (full length) enzyme or protein through a purification in which the units displaying the enzyme or protein are isolated by means of the affinity tag.

(ii) a method for in vitro selection according to the first aspect of the invention, wherein the individual units displaying (full length) enzyme or protein are purified by the means of an anti-affinity-tag antibody column in which the units displaying the tagged enzyme or protein are isolated by means of the tag.

(iii) a method for in vitro selection according to the first aspect of the invention, wherein the affinity tag comprises six histidine residues that are coupled to the C-terminal end of the enzyme or protein of interest, and the individual units displaying (full length) enzyme or protein are purified on a Ni-NTA column, or on a anti-histidine antibody column, in which the units displaying the tagged enzyme or protein are isolated by means of the tag.

Means of Isolating an Active Catalyst of Interest According to a Method of the Invention:

The separation of active and less active catalysts preferably involve a selective step during which the catalyzed reaction leads to either release or attachment of the catalyst through the linker-substrate attached to it.

There are principally four means to separate active from inactive catalysts. i) The active catalysts can be isolated by immobilization of the product on a product binding column (or more generally, by means of the attached product). ii) The inactive catalysts can be removed by immobilization on a substrate binding column. iii) Prior to the target reaction the catalyst may be attached to support; when a cleavage reaction occurs, the catalyst is released from support and can be collected. iv) The active catalysts may attach themselves to solid support upon reaction of substrate 1 (attached to the catalyst) and substrate 2 (attached to support).

The product and substrate specific columns may immobilize the product and substrate through binding to a receptor molecule with specificity for the product and substrate, respectively. Alternatively, immobilization may be mediated by a product- or substrate-specific reaction between functional groups on the column and the product or substrate attached to the catalyst.

Other means of isolating the product or substrate (and with these, the active or inactive catalysts, respectively) include partitioning between different phases, mass spectrometry, precipitation, electric or electromagnetic separation etc. In particular, electrophoresis of various kinds may be performed, especially in cases where product formation results in a significant change in the charge of the individual unit. A significant change in charge may result, for example, if the reaction is a ligation that ligates two substrates, one of which is charged and free in solution prior to the reaction substrates to product.

Accordingly, embodiments of the invention relate to (i) a method for in vitro selection according to the first aspect of the invention, wherein the selecting for a catalyst molecule of interest, in step (ii), is done by specific immobilization to said product molecule;

(ii) a method for in vitro selection according to the first aspect of the invention, wherein the selecting for a catalyst molecule of interest, in step (ii), is done by the following strategy,
  (a) constructing a system wherein substantially each of the individual units in step (i) of the first aspect comprising the substrate molecule and the catalytic molecule is bound to a matrix and wherein the unit is released from said matrix when the substrate is converted into the product; and
  (b) selecting for the unit(s) which are released from said matrix;

(iii) a method for in vitro selection according to the first aspect of the invention, wherein the selecting for a catalyst molecule of interest (step (ii)), is done by the following strategies,
  (a) constructing a product-column wherein a receptor specifically binding the product is placed along the matrix of the product-column; and
  (b) adding the sample of individual units at one end of the product-column and selecting for the catalyst molecules of interest by isolating the individual unit(s) which arrive(s) latest to the opposite end on the column;

(iv) a method for in vitro selection according to the first aspect of the invention, wherein the isolation of an entity comprising information which allows the unambiguous identification of the catalyst molecule of interest (step (iii)), is done by physical or chemical procedures; or (v) a method for in vitro selection according to the immediately above aspect, wherein the physical procedure is electrophoresis.

For a graphical illustration of point (i), (ii), and (iii) above, see FIGS. 8 and 2.

Repeating Step (i) to (iii) One or More Times, According to Point (iv) of the First Aspect of the Invention:

As stated above the term "repeating step (i) to (iii) one or more times by using the information comprised in said entity of step (iii) to generate the catalyst molecule of interest and construct an individual unit comprising said generated catalyst molecule of interest and then using this individual unit as a starting material in said repetition step" according to point (iv) in first aspect of the invention denotes that said repetition may be one time, more preferably 2 times, more preferably more than 5 times, even more preferably more than 10 times, and most preferably more than 25 times.

A Method for Producing a Catalyst Molecule of Interest, According to the Final Aspect of the Invention:

As stated above, in a final aspect the invention relates to a method for producing a catalyst molecule of interest comprising performing the method in vitro selection according to the invention and the further following steps, (a) producing said isolated catalyst molecule of interest in a suitable quantity of interest by a suitable production method.

As described above, in the method for in vitro selection, according to the first aspect the invention step (iii) reads:

"(iii) isolating an entity comprising information allowing the unambiguous identification of the catalyst molecule of interest which has been capable of catalysing multiple times the reaction substrate to product, by means of a characteristic of the product."

Accordingly, the information comprised within said entity provides the possibility of producing said catalyst molecule of interest by any standard production strategy known to the skilled person.

If said catalyst molecule of interest for instance is a polypeptide of interest said standard production strategy may be a standard protocol for recombinant production of said polypeptide of interest, or if said catalyst molecule of interest for instance is an organic molecule of interest said standard production strategies may be a standard protocol for production of such an organic molecule.

EXAMPLES

Example 1

An Example of an Individual Unit Comprising the Features of the First Aspect of the Invention.

The catalyst of interest is a SNase; the substrate is a single stranded oligonucleotide (ssDNA); and the product is the ssDNA cleaved by a SNase of interest.

Further, filamentous phage is used as a carrier system and an acid/base linker is used as a flexible linker.

Accordingly, the individual units in this example has following general structure:

SNase-fil. Phage-acid/base link.-ssDNA Catalyst-Carrier system-flexible linker-substrate. See FIG. 5 for an illustration.

In this example the "selection characteristic" of the product (i.e. cleaved ssDNA) is that said product does not bind to a matrix and the substrate (ssDNA) does bind to a matrix.

Accordingly, in this example a SNase molecule of interest is isolated by selecting for individual units which are released from said matrix. See FIG. 5 for an illustration.

Materials and Methods.

Synthesis of compounds. Fmoc-S-(2-nitro-4,5-dimethoxybenzyl)-L-cysteine 1 was synthesized by a variation of the method of Merrifield (6). Briefly, 605 mg L-cysteine (5 mmol) was suspended in 100 mL degassed ethanol/water (2:1), and 1.39 mL triethylamine (10 mmol) and 1.39 g 1-(bromomethyl)-2-nitro-4,5-dimethoxybenzene (5 mmol) were added. The mixture was stirred for 10 h at 23° C. in the dark under nitrogen and filtered. The filter cake was washed with ethanol and recrystallized from ethanol/water to provide 0.95 g S-(2-nitro-4,5-dimethoxybenzyl)-L-cysteine (3 mmol). The recrystallized product (0.8 g) was suspended in 20 ml water; 0.53 ml triethylamine (3.8 mmol) was added followed by a solution of 0.9 g 9-fluorenylmethoxycarbonyl succinate ester (2.7 mmol) in 12 mL acetonitrile and the mixture stirred for 10 h at 25° C. under nitrogen. The product precipitated upon acidification to pH 2–3 with 1 M HCl and evaporation of the acetonitrile. The precipitate was collected on a frit and washed with water and ethylacetate to remove excess HCl and reagent. The resulting crude product 1 (1.13 g) was extensively dried under vacuum, and used directly in the synthesis of the base-linker peptide C(GGS)$_4$ AQLKKKLQALKKKNAQLKWKLQALKK-KLAQGGC (SEQ ID NO:1) (base sequence underlined, photoprotected cysteine in bold). Compounds 2, 3 and 4 were synthesized on an ABI DNA synthesizer on a 1 mmole scale with a 3'-biotin group (BiotinTEG CPG, Glen Research) and a 5'-thiol (5'-Thiol-Modifier C6, Glen Research) and purified by reverse phase HPLC following removal from the resin (Rainin Microsorb C18 column, flow 1 mL/min.; solvent A: 50 mM triethylammonium acetate (TEAA), pH 7, solvent B: acetonitrile, linear gradient from 5 to 50% solvent B over 40 min); the trityl protecting group on the thiol was removed according to the protocol of Glen Research. The products were lyophilized and dissolved in water (1.0 mM final concentration). The conjugate of 2 with the base-linker peptide was prepared as follows: 2 mg (415 nmole) base-linker peptide was reacted with a 20 fold molar excess of N,N'-bis(3-maleimidopropionyl)-2-hydroxy-1,3-propanediamine (3.2 mg) in 1 mL of 50 mM sodium phosphate buffer, pH 5.5, for 10 h under nitrogen at 4° C. Compound 5 was purified from the reaction mixture by reverse phase HPLC (Vydac RP-18 column, flow 2 mL/min; solvent A: 0.1% TFA in water, solvent B: 0.1% TFA in acetonitrile; linear gradient from 10 to 55% solvent B over 35 minutes), and the product fractions concentrated to approximately 0.3 mL (OD$_{280}$=6, compound 5 should not be concentrated to dryness). To 100 mL (138 nmoles) of this solution was added 75 ul water, 75 mL of aqueous 1 M aqueous sodium phosphate, pH 7, 30 mL of aqueous 5 M NaCl, and 22 mL (22 nmoles) of compound 2, and the reaction incubated for 10 h under nitrogen at 23° C. (to avoid precipitation the reagents should be added in this order). The product was purified by anion exchange FPLC (Mono Q HR 5/5 column (Pharmacia), flow 0.75 mL/min solvent A: 20 mM Tris-HCl, pH 7, solvent B: 20 mM Tris-HCl, pH 7, 2 M NaCl; linear gradient from 20 to 60% B in 7.5 min); on a 10% denaturing polyacrylamide gel the product ran as a single band. Fractions of OD$_{260}$=0.3–1 were used directly for the photo-deprotection step (vide infra). The conjugates of 3 and 4 with the base-linker-peptide were prepared as follows: approximately 200 nmoles of either 3 or 4, and a 20 fold excess of bismaleimide were incubated in 1 mL of aqueous 50 mM phosphate buffer, pH 5.5, at 4° C. for 15 hours. After purification by reverse phase HPLC and lyophilization, the identity of compounds 6 and 7 was verified by Maldi-ToF MS. Either 6 or 7 (150 nmoles) was then incubated with 100 nmoles base-linker-peptide in 100 mL of 10 mM TEAA, pH 6.5, 100 mM NaCl for 15 hours at 4° C. The products were purified by reverse phase HPLC (Vydac RP-18 column, conditions as described above), lyophilized and analyzed by Maldi-ToF MS (7). The 2-nitro-4,5-dimethoxybenzyl protecting group on the C-terminal cysteine of the three conjugates was removed by photolysis to afford compounds 8, 9 and 10 as follows: for compound 8, 100 mL of the FPLC purified fraction containing the protected conjugate (vide supra) was degassed thoroughly with argon for 15 min, and then exposed to a mercury lamp (450 W high pressure mercury lamp, Ace-Hanovia; Pyrex™ filter, cutoff $^2$ 300 nm) in a septum capped glass vial for 30 min (8). For compounds 9 and 10, 10 nmole of the conjugate was dissolved in 100 mL of 10 mM DTT, degassed and photolyzed as described above. After 30 min of irradiation no remaining starting material could be detected by MALDI-ToF MS. The reaction mixture was separated by HPLC (Vydac RP-18 column, conditions as described above) and the product fractions were lyophilized. The conjugates were stored frozen, and used within a week after photo-deprotection, to ensure efficient attachment to phage.

Construction of acid helper phage. A NarI restriction site was introduced between the third and fourth codon of mature pIII protein of M13K07 helper phage (Promega) by Kunkel mutagenesis (9) with the primer K07-NarI-prim (5'-ACAACTTTCAACGGCGCCAGTTTCAGCGG-3') (SEQ ID NO:2) to give NarI-helper phage. DNA encoding the amino acids GA AQLEKELQALEKENAQLEWELQALEKELAQ-GGCP AGA (SEQ ID NO:3) (acid peptide sequence underlined, GGC motif in bold) with a NarI restriction site at both ends, was produced by polymerase chain reaction (PCR) with the plasmid pCRII acid (Ellis L. Reinherz, Dana Farber Cancer Institute, Boston) with the primers NarIfwd (5'-ACTACAAATTGGCGCCGCTCAGCTCGAAAAAGA GC-3') (SEQ ID NO:4) and NarIbck (5'-AATTATAGGCGCCAGCCGGGCAACCGCCCTGAGC CAGTTCCTTTTCC-3'). (SEQ ID NO:5) The PCR product was digested with NarI and inserted into NarI digested NarI-helper phage to afford acid helper phage.

Construction of phagemids encoding the staphylococcal nuclease-p-III fusion and 39-A11 Fab-pIII fusions. To make the SNase-pIII fusion, PCR was performed on the plasmid pONF1 (10), carrying the gene encoding SNase, with primers 5'-CGCGAATTG GCCCAGCCGGCCATGGCCGCAACTTCAACTAAA-3' (SEQ ID NO:6) (SfiI restriction site underlined and 5'-GCGAATTGGT GCGGCCGCTTGACCTGA-ATCAGCGTTG-3' (SEQ ID NO:7) (NotI restriction site underlined). The product was digested with SfiI and NotI and inserted into SfiI-NotI digested pFAB-5c.His, a derivative of plasmid pFAB-5c (11), to give phagemid pII78-6. As a negative control the phagemid pComb3H.DA was employed. This phagemid (12) carries the 39-A11 Fab antibody (13) fused to the pIII protein. The expression of both the SNase and control protein is driven by the lac promoter.

Production of phage particles. Phage particles were produced with minor modifications according to Ørum et al. (11). Briefly, *E. coli* XL1-blue was transformed with pII78-6 or pComb3H.DA, and shaken at 37° C. in 2×YT broth and 100 mg/mL ampicillin. At an $OD_{600}$ of 0.5, acid helper phage was added to a final concentration of $1.5 \times 10^8$ cfu/mL, and incubated at 37° C. for 20 min. The cells were pelleted and resuspended in 2×YT, 100 mM IPTG, 100 mg/mL ampicillin, 50 mg/mL kanamycin, and shaken for 14 hours at RT. Cells were pelleted and phage particles in the supernatant were PEG precipitated, followed by resuspension in TBS (25 mM Tris-HCl, pH 7.4, 140 mM NaCl, 2.5 mM KCl). Phage titrations were performed with *E. coli* XL1-blue using standard procedures (14).

Covalent Attachment of Base-Linker-Substrate Conjugates to Phage.

Approximately $10^8$ phage particles were incubated in 40 mL buffer A (TBS, 10 mM EDTA, 0.1% BSA), supplemented with 1 mM mercaptoethylamine (MEA) and 1 nmole of either base-linker-oligodeoxynucleotide (8), base-linker-pTp (9) or base-linker-pTpTp (10), at 37° C. for 60 minutes, then PEG precipitated twice and resuspended in buffer A.

Phage immobilization and release from solid support. Approximately $10^8$ phage particles, covalently attached to the base-linker-substrate conjugates, were incubated with 50 mL magnetic streptavidin beads (Boehringer Mannheim, biotin binding capacity: 1.5 nmole/mL) in 1 mL buffer A for 15 minutes at 23° C.; eight 1 min washes were performed in buffer A with 0.1% Tween 20, followed by two 1 min washes in buffer A. The number of phage immobilized on the beads was determined by suspending the beads in buffer A, and then either directly infecting *E. coli* XL1-blue with the bead suspension and titering or alternatively, infecting after treatment of the beads with DNase 1 (1 unit/mL DNase 1, 10 mM $MgCl_2$, 20 mM Tris-HCl, pH 8, 23° C. for 15 min). Calcium-dependent release (cleavage) from solid support was examined by suspending beads in buffer B (TBS, 10 mM $CaCl_2$, 0.1% BSA), incubating at 23° C. for 5 min, and titering the supernatant. Calcium-independent release from the beads (leakage) was determined by resuspending the beads in buffer A, incubating for five minutes at 23° C., and titering the supernatant.

Enrichment of active enzymes from a library-like ensemble. Phage particles displaying SNase or 39-A11 Fab were mixed in a 1:100 ratio and the base-linker-oligodeoxynucleotide conjugate (8) was covalently attached. Phage were then immobilized on magnetic streptavidin beads, washed in buffer A, and incubated in buffer B as described above, *E. coli* XL1-blue were infected with the supernatant and the cells plated on a LA plate containing 100 mg/mL ampicillin. Randomly picked colonies were identified as SNase- or control clones by PCR or restriction enzyme digestion.

Results & Discussion.

Selection scheme. To test the above strategy for directed-enzyme evolution in a phage-display format, it was first necessary to develop a general method for selectively attaching a given substrate to or near a phage-displayed enzyme. Importantly, the substrate must be attached so that it can bind productively in the active site of the conjugated enzyme. Moreover, the substrate should be covalently linked to the phage to ensure that there is no crossover of reaction product between members of the library. One possible strategy involves selective chemical modification of the enzyme or a nearby phage coat protein (e.g., pIII protein) with substrate by a disulfide exchange reaction. For example, a cysteine residue introduced near the active site of staphylococcal nuclease through site-directed mutagenesis has been used to selectively introduce unique chemical functionality by a disulfide exchange reaction (15). To apply this method to proteins expressed on filamentous phage, the three single cysteines of the pVI, pVII and pIX coat proteins were first mutagenized to alanine. The eight buried cysteine residues in the pIII protein were left unchanged, as they likely form structurally important disulfide bridges (16). Unfortunately, repeated attempts to selectively modify unique cysteine residues introduced near the active site of several enzymes displayed on phage, by either disulfide exchange, maleimide addition or alkylation reactions, resulted in significant nonspecific labelling of phage coat proteins. No conditions or reagents were found that made possible selective labelling of the pIII fusion protein containing the unique surface cysteine residue. It is likely that the thousands of proteins constituting the phage coat make the specificity requirement for a chemical reaction too great; also, the probability of cysteine misincorporation due to the intrinsic error rate in protein biosynthesis becomes significant for such a large ensemble of proteins. Alternatively, the cysteine residues in the pIII protein may be accessible to crosslinking reagents.

To circumvent these problems, a two step process was developed in which chemical crosslinking is preceded by the selective formation of a noncovalent complex at the site of modification (FIGS. 4 and 5). The complex is a heterodimeric coiled-coil consisting of a synthetic basic peptide B $C(GGS)_4$ AQLKKKLQALKKKNAQLKWKLQALKKKLAQGGC, (SEQ ID NO:1) to which substrate is covalently coupled before heterodimerization, and an acidic peptide A, GA AQLEKELQALEKENAQLEWELQALEKELAQGGCP AGA (SEQ ID NO:8) that is expressed as an N-terminal fusion to the pIII coat protein of filamentous phage. The acid and base peptides (underlined) were chosen as dimerization domains because of their small size (thirty amino acids) and high tendency to form stable, parallel heterodimeric coiled-coil structures—the acid—acid and base—base homodimers form $10^5$ fold less efficiently than the heterodimer (17). Heterodimerization of the synthetic (B) and phage-encoded (A) peptides should bring the substrate into close proximity of the displayed enzyme, and lead to spontaneous disulfide bond formation between cysteines on each of the peptides (FIG. 5). The tripeptide Gly-Gly-Cys was added to the C-termini of the acid and base peptides to facilitate formation of a disulfide bridge between the two helices (17). The substrate is covalently linked to the basic peptide B through a flexible linker to facilitate productive binding of substrate to enzyme (FIG. 4). The acidic peptide A is fused to the pIII protein of the phage rather than to the displayed enzyme itself for the following reasons: (i) insertion of the acid peptide sequence into an enzyme might interfere with enzyme function; (ii) the flexible linker of the base-linker-peptide as well as hinges in the pIII protein and a peptide linker inserted between pIII and the displayed enzyme, should allow many possible orientations of the substrate relative to the enzyme active site; and (iii) it should be possible to use a single helper phage bearing the acid peptide extension to display many enzyme-substrate pairs, rather than having to engineer into each enzyme a functional conjugation site.

Generation of the Acid Helper Phage and Base-Linker-Substrate Conjugate.

To attach the base-linker-substrate conjugate to phage we introduced the acidic peptide A at the N-terminus of pIII protein in the M13K07 helper phage. The enzyme library is fused to the N-terminus of the pIII coat protein; this construct is carried in the phagemid. Upon superinfection by helper phage, phage particles are produced that contain the phagemid DNA but whose coat consists (with one exception) of proteins encoded by the helper phage genome. The one exception is the pIII protein, present in 4–5 copies at one tip of the phage. During packaging of the phage, both enzyme-pIII fusions and acid peptide A-pIII fusions are produced; the phage particles obtained from a typical preparation carry either one or zero enzyme-pIII fusions plus three to five copies of acid peptide A-pIII fusion.

To generate phages bearing an acid peptide-pIII fusion, DNA encoding the acidic peptide A with a C-terminal extension containing a cysteine residue, was introduced into the 5'-end of gene III of the M13K07 helper phage. The resulting acid helper phage particles were immoblized more than hundred fold more efficiently than M13K07 on an ELISA-plate coated with basic peptide B, indicating that the mutant helper phage carry accessible acid peptide extensions on their pIII proteins. Likewise, when $E.\ coli$ containing a phagemid encoding a pIII fusion protein were superinfected with the acid helper phage, the resulting phage particles displayed modified pIII extensions in addition to the pIII fusion protein (FIG. 5). The insertion of the acid peptide did not appear to change the titer or rescue efficiency of the helper phage significantly.

The synthetic base-linker-peptide (B) to which substrate is attached consists of the twelve residue (GlyGlySer)$_4$ (SEQ ID NO:1) linker followed by the thirty amino acids constituting the base sequence (FIG. 4). The base-linker peptide also contains cysteine residues at the N-and C-termini that allow efficient, selective coupling of the peptide to substrates and disulfide bond formation to phage, respectively (FIGS. 4 and 5). The C-terminal cysteine of the synthetic peptide is initially protected with the photochemically removable 2-nitro-4,5-dimethoxybenzyl protecting group. This allows substrate to be selectively conjugated by a thiol specific reaction (e.g., by disulfide exchange, alkylation, or Michael addition reactions) to the free thiol group of the N-terminal cysteine. After substrate conjugation, the C-terminal cysteine is photochemically deprotected in high yield to generate a free thiol available for crosslinking to the acid peptide extension on phage. Because the chemical conjugation of substrate and base-linker peptide, and the crosslinking of this conjugate to phage are carried out separately, many different chemistries and reaction conditions can be used to couple the base-linker peptide and substrate. Moreover, the composition of the conjugate can be purified and characterized (e.g., by mass spectrometry) before it is crosslinked to phage.

Staphylococcal nuclease as a model system. The enzyme staphylococcal nuclease is a well-characterized enzyme consisting of a single polypeptide chain 149 amino acids in length (18). The enzyme preferentially hydrolyzes the phosphodiester bonds of single-stranded RNA (ssRNA), ssDNA, and duplex DNA at A,U- or A,T-rich regions to generate 3'-phosphate and 5'-hydroxyl termini (18). $Ca^{2+}$ is required for enzymatic activity, providing a mechanism for modulating enzyme action. In addition, SNase has successfully been displayed as a pIII fusion protein on phage (19).

Because no reagent, antibody or receptor is available that can easily distinguish between a single-stranded oligodeoxynucleotide substrate and its cleavage product (a complementary oligonucleotide would be degraded), a selection scheme was developed in which enzymatic cleavage of ssDNA substrate results in release of phage from solid support. In this scheme, one round of selection involves the following steps: i) attachment of phage displaying SNase to solid support through a single-stranded oligodeoxynucleotide (in the absence of $Ca^{2+}$ to inactivate SNase); ii) removal of unbound phage by washing; iii) initiation of the cleavage reaction by addition of $Ca^{2+}$, and iv) isolation of eluted phage. In later rounds of selection, elution can be done under increasingly stringent conditions, eg., shorter reaction time, lower temperature and altered pH. Attachment of phage to solid support is carried out by coiled-coil formation between 5'-biotinylated oligodeoxynucleotide-peptide B conjugates and acid peptide A extensions on phage, followed by disulfide crosslinking of the two peptides and immobilization on streptavidin beads (FIG. 4). This scheme, in which the phage is attached to solid support through the substrate, requires that the enzyme or substrate be maintained in an inactive state during attachment to phage, and then be activated by a change in reaction conditions. Such changes can include modulation of pH, addition of cofactors or co-substrates, and photochemical or chemical activation of the substrate. In the case of biomolecular condensation reactions in which bond formation results in phage immobilization on solid support, it is not necessary to initiate the reaction; the same is true if capture of active enzymes is by a product-specific reagent, antibody or receptor.

Covalent attachment of the substrate to phage. Phage displaying either SNase or a control protein (antibody 39-A11 Fab fragment) were prepared by superinfection with the acid helper phage. To evaluate the efficiency of the attachment of base-linker-substrate conjugates to phage, an excess of a control conjugate, "pTp"-peptide B (compound 9), was incubated with the phage. The base-linker-pTp conjugate consists of a biotin moiety, followed by deoxythymidine-3',5-diphosphate (pTp), the flexible peptide linker and base peptide sequence, and a C-terminal cysteine. The base-linker-pTp conjugate is not a substrate for wild-type SNase in solution (pTp is a potent inhibitor of SNase) (20). Phage and the substrate-peptide B conjugate were first incubated with the reducing agent mercaptoethylamine (MEA) to reduce disulfide bonds between cysteines on the phage acid peptide or the synthetic peptide. Then, MEA and free base-linker-pTp were removed by PEG precipitation, and magnetic streptavidin beads were added. After ten washes, the number of phage that were immobilized was determined by infection of $E.\ coli$ XL1-blue with the beads, and titering phage. When measured this way, the efficiency of phage immobilization was approximately 10%, for both phage displaying SNase and 39-A11 Fab (FIG. 6).

Next it was determined whether an oligodeoxynucleotide substrate attached to phage displaying SNase would be stable in the absence of $Ca^{2+}$. The base-linker-oligodeoxynucleotide conjugate was attached to phage displaying SNase (in the presence of EDTA), and the immobilization efficiency determined as above. The efficiency of immobilization was again approximately 10% (FIG. 6), indicating that the tethered oligodeoxynucleotide substrate is not cleaved by SNase in the absence of $Ca^{2+}$. It is possible that the true immobilization efficiency is higher than observed if some of the phage are rendered non-infective when attached to the beads. This notion was tested by addition of DNase I, which should cleave the tethered oligodeoxynucleotide substrate and release the immobilized phage. As can be seen in FIG. 6, most of the immobilized phage are non-infective, but become infective upon addition of DNase I, indicating that the true immobilization efficiency is about 80% (FIG. 6). If the oligodeoxynucleotide-peptide B conjugate is not included, less than 0.01% of the phage become immobilized; if the wildtype M13K07 helper phage is used to superinfect, about 0.3% of phage are immobilized. It thus appears that the two-step protocol for attachment of substrate to phage pIII protein is efficient and highly site-specific.

Enzyme dependent cleavage of phage from solid support and enrichment. To determine whether phage-displayed SNase is capable of specifically cleaving the tethered oligodeoxynucleotide substrate in an intramolecular reaction, $Ca^{2+}$ was added to the immobilized phage to activate the enzyme. Approximately 15% of the phage were released (FIG. 6), in contrast to release of only 0.2% of the control phage displaying Fab 39-A11 (FIG. 6). This experiment demonstrates that SNase cleaves and releases phage from the solid support much more efficiently than the control protein, as expected. However, it appears that a small but significant fraction of the phage leak off the support during the assay (this background leakage is observed without $Ca^{2+}$, for both the base-linker-oligodeoxynucleotide and base-linker-pTp conjugates, and for both displayed proteins, FIG. 6. Addition of $Ca^{2+}$ leads to an initial burst of phage release from support; however, the release of phage quickly declines to a level corresponding to the leakage observed without $Ca^{2+}$. This result demonstrates that phage released into solution by intramolecular cleavage events do not release other phage from support as a result of intermolecular cleavage reaction. Cross-reactivity therefore does not appear to be significant, even with a very active enzyme like SNase.

The above analysis suggests that it should be possible to enrich phage displaying SNase from a library-like ensemble of phage displaying catalytically inactive proteins. To test this, phage displaying SNase and the Fab 39A-11 control protein were mixed in a ratio of 1:100, crosslinked to the oligodeoxynucleotide-peptide B conjugate and immobilized. After incubation with $Ca^{2+}$, the ratio of recovered phage was 22:18, which corresponds to an enrichment factor slightly higher than 100. This degree of enrichment should be sufficient to isolate an active catalyst from a library of $10^{10}$ members after five rounds of selection and amplification.

The enrichment factor can likely be increased by minimizing background leakage of phage from support. This leakage may result from release of streptavidin from support, or alternatively, reduction or incorrect formation of the disulfide bridge between the synthetic and phage encoded peptides. We are currently exploring these possibilities. Alternatively, the enrichment factor can be increased by increasing the extent of the enzyme-catalyzed cleavage reaction. Under the conditions of phage production, the ratio of pIII expressed from the helper phage relative to the pIII fusion protein expressed from the phagemid is such that most of the phage carry only wildtype pIII proteins; only a minor fraction of the phage carry the protein-pIII fusion. The number of phage that can cleave themselves off can be increased simply by increasing the number of phage that display the enzyme. For the phagemid/helper phage combination described here, we estimate that only about 15% of the phage are monovalent. By appropriate vector design and phage preparation, it should be possible to increase the average display to about one protein per phage. This should increase the cleavage to leakage ratio 7 fold, and hence, increase the enrichment factor of active versus inactive enzymes from the present ~100 to about 700.

To examine whether the selection scheme described here can be used for reactions that involve small molecule substrates, a pTpTp-peptide B conjugate (compound 10) was attached to phage displaying SNase or the control protein. Phage were carried through the enrichment routine described above, and again SNase displaying phages were enriched. MALDI-TOF mass spectrometry was used to show that the pTpTp substrate was cleaved at the phosphodiester bond between the two thymidines; no side products were detected. It thus appears that the methodology is applicable to both macromolecular and small molecule substrates. We are currently exploring the possibilities for isolating novel catalysts from libraries of enzyme or antibody origin.

Most enzyme libraries displayed on phage require superinfection by a helper phage like M13K07. The selection protocol described here can therefore be applied directly to these libraries—one simply needs to prepare phage after superinfection of the phagemid encoded library with the acid peptide helper phage, and conjugate the substrate of choice to the basic peptide B. Likewise, this methodology can be applied to populations of structurally diverse proteins. The collection of proteins encoded by a genome is one such population. For example, it should be possible to isolate natural kinases with predefined substrate specificity from a genomic protein library using this selection scheme. This type of functional cloning in which a natural enzyme (and the gene that encodes it) is isolated on the basis of its catalytic activity should be applicable to many reactions catalyzed by natural enzymes.

REFERENCES AND NOTES USED IN EXAMPLE 1

1. Schultz, P. G. & Lerner, R. A. (1995) *Science* 269, 1835–1842.
2. (a) Marks, J. D., Hoogenboom, H. R., Bonnert, T. P., McCafferty, J., Griffiths, A. D. & Winter, G. (1991) *J. Mol. Biol.* 222, 581–597. (b) Barbas, C. F., III, Bain, J. D., Hoekstra, D. M. & Lerner, R. A. (1992) *Proc. Natl. Acad. Sci. U.S.A.* 89, 4457–4461. (c) Griffiths, A. D., et al. (1994) *EMBO J.* 13, 3245–3260.
3. Janda, K. D., Lo, C-H. L., Li, T., Barbas, C. F., III, Wirsching, P. & Lerner, R. A. (1994) *Proc. Natl. Acad. Sci. U.S.A.* 91, 2532–2536.
4. (a) Soumillion, P., Jespers, L., Bouchet, M., Marchand-Brynaert, J., Winter, G. & Fastrez, J. (1994) *J. Mol. Biol.* 237, 415–422. (b) Janda, K. D., Lo, L-C., Lo, C-H. L., Sim, M. M., Wang, R., Wong, C-H. & Lerner, R. A. (1997) *Science* 275, 945.
5. Gao, C., Lin, C. H., Lo, C-H. L., Mao, S., Wirsching, P., Lerner, R. A. & Janda, K. D. (1997) *Proc. Natl. Acad. Sci. U.S.A.* 94, 11777–11782.
6. Erickson, B. W. & Merrifield, R. B. (1973) *J. Am. Chem. Soc.* 95, 3750–3756.
7. Piles, U., Zürcher, W., Schär, M. & Moser, H. E. (1993) *Nucl. Acids. Res.* 21, 3191–3196.
8. Marriott, G. & Heidecker, M. *Biochem.* (1994) 33, 9092–9097.
9. Kunkel, T. A., Roberts, J. D. & Zakour, R. A. (1987) Methods in Enzymology 154, 369.
10. Hibler, D. W., Barr, P. J., Gerlt, J. A. & Inouye, M. (1985) *J. Biol. Chem.* 260, 2670–2674.
11. Ørum, H., Andersen, P. S., Øster, A., Johansen, L. K., Riise, E., Bjørnvad, M. Svendsen, I. & Engberg. J. (1993) *Nucl. Acids Res.* 21, 4491–4498.
12. Schultz, P. G. & Romesberg, F. E. unpublished results.
13. Romesberg, F. E., Spiller, B., Schultz, P. G. & Stevens, R. C. (1998) *Science* 279, 1929–1933.
14. Sambrook, J., Fritsch, E. F. & Maniatis, T. (1989) "Molecular Cloning: A Laboratory Manual," 2nd Ed. Cold Spring Harbor Lab., Cold Spring Harbor, N.Y.

15. Pei, D., Corey, D. R. & Schultz, P. G. (1990) *Proc. Natl. Acad. Sci.* 87, 9858–9862.
16. (a) Lubkowski, J., Hennecke, F., Plückthun, A. & Wlodawer, A. (1998) *Nature Structural Biology* 5, 140–147. (b) Kremser, A. & Rasched, I. (1994) *Biochemistry* 33, 13954–13958.
17. (a) O'Shea, E. K., Rutkowski, R., Kim, P. S. (1989) *Science* 243, 538–542. (b) O'Shea, E. K., Rutkowski, R., Stafford, W. F. III & Kim, P. S. (1989) *Science* 245, 646–648. (c) O'Shea, E. K., Klemm, J. D., Kim, P. S. & Alber, T. (1991) *Science* 254, 539–544. (d) xZhou, N. E., Kay, C. M. & Hodges, R. S. (1993) *Biochemistry* 32, 3178–3187.
18. (a) Cotton, F. A., Hazen, E. E., Jr., & Legg, M. J. (1979) *Proc. Natl. Acad. Sci. U.S.A.* 76, 2551–2555. (b) Tucker, P. W., Hazen, E. E., & Cotton, F. A. (1978) *Mol. Cell. Biochem.* 22, 67–77. (c) Sondek, J. & Shortle, D. (1990) *Proteins* 7, 299–305. (d) Hale, S. P., Poole, L. B. & Gerlt, J. A. (1993) *Biochemistry*, 32, 7479–7487. (e) Hynes, T. R. & Fox, R. O. (1991) *Proteins* 10, 92–105. (f) Loll, P. J., Quirk, S., Lattman, E. E. & Gravito, R. M. (1995) *Biochem.* 34, 4316–4324. (g) Judice, K., Gamble, T. R., Murphy, E. C., de Vos, A. M. & Schultz, P. G. (1993) *Science* 261, 1578–1581.
19. Ku, J. & Schultz, P. G. (1994) *Biomed. Chem. Lett.* 2, 1413–1415.
20. Tucker, P. W., Hazen, E. E., Jr. & Cotton, F. A. (1979) *Mol. & Cell. Biochem.* 23, 3–16.

Example 2
Optimization of an Enzyme with Glycosidase Activity.

This is an example of the selection scheme depicted in FIG. 7. An enzyme with glycosidase activity is displayed on the surface of a filamentous phage using the principles described in example 1 above and the skilled person's general knowledge.

The substrate is a glycogen linker substrate attached to the surface of a filamentous phage using the principles described in example 1 above and the skilled person's general knowledge.

Further, the enzymes are attached to column through the glykogen linker by standard techniques known in the art.

Enzymes with the desired catalytic activity will cleave the bond between the two sugars, releasing the phage with a glucose unit attached to it. However, glycogen synthase present in the buffer will catalyze the condensation of glucose and UDP-glucose, and as a result reattach the enzyme to the column through a portion of glycogen. Enzymes with the highest catalytic efficiency will flow through the column the fastest, and can be collected from the first column fractions.

Example 3
An Example of an Individual Unit Comprising the Features of the First Aspect of the Invention.

In the following it is described how the substrate may be attached to an enzyme in a plasmid-peptide system (Schatz et al., 1996, Meth. Enzym., vol. 267, pp. 171–191), polysome-peptide system (Mattheakis et al., 1994, Proc. Natl. Acad. Sci. USA, vol. 91, pp. 9022–9026; He and Taussig, 1997, Nucleic Acids Research, vol. 25, pp. 5132–5134) or mRNA-peptide system (Roberts and Szostak, 1997, Proc. Natl. Acad. Sci. USA, vol. 94, pp. 12297–12302). Here exemplified with the mRNA-peptide fusion system.

Design the template DNA so as to make a portion of the mRNA in the mRNA-protein fusion an annealing site for another oligo (eg. include the DNA sequence 5'-GCCGAAGCGCAATGAAGGGC-3' (SEQ ID NO:9) in the template DNA). Attach desired substrate to a DNA oligo complementary to the sequence above (ie. 3'-CGGCTTCGCGTTACTTCCCG-5' (SEQ ID NO:10). Then after preparation of the mRNA-peptide fusion, mix the mRNA-peptide fusion and the substrate conjugate, and perform substrate reloading selection, for example by applying the mix to a product binding column as described above (see FIG. 9A).

Alternatively, the linker that connects the mRNA and the encoded peptide can carry the sequence 5'-GCCGAAGCGCAATGAAGGGCAACCCG-3' (SEQ ID NO:11). Then mix the substrate-DNA conjugate (where the DNA is complementary to DNA in the linker) and perform substrate reloading selection as described above (see FIG. 9B).

Example 4
Optimization of a Secreted Enzyme's Activity.

This is an example of the selection scheme outlined in FIG. 8. The individual unit consists of a cell, a substrate attached to the surface of that cell, and enzymes produced and secreted by the cell (FIG. 11). The substrate is attached to the surface of an enzyme-secreting cell through a linker. Reagent(s) in the media continuously turn product (produced by the secreted enzymes) into substrate. Consequently, as the local concentration of secreted enzyme is much higher near the substrate attached to the cell from which it was secreted than near any of the other cells' attached substrates, there will be more product attached on a cell secreting an active enzyme than on a cell secreting a less active enzyme.

The substrate can be attached to the cell surface in many ways. For example, phospholipids, fatty acids, sterols or cholesteryl esters may be derivatized with the substrate of the target reaction. When incubated with cells, these carbon chains readily localize in the membrane interior, and expose the substrate on the surface of the cell. Alternatively, the substrate may be derivatized with crosslinking reagents that react with the surface constituents. Finally, the substrate may be conjugated to structures (e.g. proteins, antibodies) that bind to membrane components such as polysaccharides or membrane proteins.

The principle is here exemplified in the case where the individual unit consists of a cell (bacteria or yeast), attached substrate (double stranded DNA with 5'-overhang), and secreted enzyme (ligase; for example, in a recombinant form that allows its secretion). A restriction enzyme (for example EcoRI) is used as the reagent. The selection is performed in the column format. The column matrix is coated with double stranded DNA with 5'-overhangs that are complementary to the overhangs exposed on the surface of the cell, and that create an EcoRI restriction site upon ligation of the two DNA fragments.

DNA substrate is attached to the cells as follows. A PCR reaction is performed, using two primers one of which is 5, derivatized with N-hydroxysuccinimide, and DNA containing an EcoRI restriction site as template. Approximately 50 μg DNA product is digested with EcoRI and purified, to yield a 10–100 base pair double stranded DNA with EcoRI 5'-overhangs at one end, and the N-hydroxysuccinimide moiety at the other. The DNA is mixed with cells, harvested at the exponential growth phase and resuspended in appropriate buffer. This results in the reaction of primary amines on the surface of the cell with the N-hydroxysuccinimide moiety of the DNA. As a result, the DNA becomes covalently attached to the cell surface.

A DNA column is made as follows. A PCR reaction is performed, using a biotinylated and a non-biotinylated primer, and a DNA containing an EcoRI restriction site is used as template. The PCR product is cleaved with EcoRI, to produce a fragment of 10–100 base pairs. The fragment is mixed with streptavidin-coated Sepharose or Sephadex column material.

The DNA coated cells are loaded on the DNA column, together with the restriction enzyme (EcoRI), in a suitable buffer that allows activity of both the restriction enzyme and the ligase (i.e. contains ATP, pH 7–9), as well as allows efficient secretion of the ligase. The temperature is 24–37° C.; the flow is kept below 0.5 mL/min.

Cells secreting an active ligase become immobilized on the column, through ligation of the complementary DNA overhangs of the cell surface and the column. Upon ligation, EcoRI will cleave the DNA and thereby release the cell from the column matrix. Consequently, cells secreting active ligase will migrate slower through the column; cells secreting very active ligases may not migrate through the column at all. Therefore, cells secreting the more active ligase is isolated from the later column fractions, or may be eluted from the column matrix, for example by addition of high concentrations of DNase.

The principle is tested by isolating the cells that secrete the most active ligase/highest expressed ligase from a model library of well characterized cell clones.

The stringency of the selection is controlled by the density of DNA fragments on the surface of the cell and solid support, as well as by the concentration of the restriction enzyme in the buffer. Ligase variants with improved characteristics at desired pH, salt and temperature conditions may be evolved by this method. Also, the inverse experiment may be performed; using ligase and ATP as the reloading reagents, and conditions similar to those described above, and cells secreting restriction enzymes, it may be possible to isolate restriction enzymes that cleave novel targets, or that cleave under different conditions.

Example 5

Enrichment of Wildtype RNaseA Peptide on Beads, in a Background of Excess, Less Active RNase A Peptide Variants, Using RNA Ligase, Polynucleotide Kinase and ATP as the Reagents In order to test the substrate reloading principle in the field of synthetic combinatorial chemistry, we have designed a simple experiment involving the RNase A peptide. Two C-terminally biotinylated peptides, Peptide1 and Peptide2, are synthesized, for example as outlined in (Gutte et al., 1971, Journal of Biological Chemistry, vol. 246, pp. 1922–1941). Peptide1 carries wildtype RNase A. Peptide 2 has the same sequence as Peptide1, except that mutation(s) have been introduced that fully or partly eliminates the ribonuclease activity of the peptide (for example by replacing one or both of the two active site histidines, H12 and H119, with Alanine). After deprotection and cleavage from the synthesis support, the RNase A peptide variants are refolded as described in (Gutte et al., 1971, Journal of Biological Chemistry, vol. 246, pp. 1922–1941).

A 5'-biotinylated DNA/RNA hybrid (20–30 nucleotides; 3–10 nucleotides at the 3' end are ribonucleotides, the rest are deoxy-ribonucleotides (Oligos Etc., Inc.)), is mixed with either Peptide1 or Peptide2, and the peptides and nucleic acids are immobilized on streptavidin coated beads of approximate diameter 10–100 nm through their biotin moieties. Such beads may be prepared by immobilizing streptavidin to N-hydroxy-succinimide-activated Latex beads (Polysciences Inc.).

A 3'-thiolated DNA/RNA hybrid of 20–30 nucleotides, of which 3–10 nucleotides at the 5'-end are ribonucleotides, and the rest are deoxyribonucleotides, is synthesized with a 5'-phosphate (Oligos Etc., Inc.). The thiolated DNA/RNA hybrid is coupled to a column matrix carrying activated disulfide (for example activated as a pyridyl-disulfide).

A substrate reloading experiment is now performed as follows (see FIG. 10). The mix of beads carrying the DNA/RNA hybrid and either Peptide1 or Peptide2, respectively, is mixed in a buffer in which both RNase A, RNA ligase and polynucleotide kinase is active (thus, the buffer should include $MgCl_2$ and ATP). The mix is loaded on the DNA/RNA-conjugated column described above, together with RNA ligase (New England Biolabs) and T4 polynucleotide kinase (New England Biolabs) at 37° C. The column is washed with the same buffer for several column volumes, and fractions collected. During their migration through the column, the Peptide1 beads (carrying wildtype RNase A) will become immobilized to the column matrix through the ligation by the RNA ligase of the 3'-hydroxyl of the DNA/RNA attached to the Peptide1 beads and the 5'-phosphate of the DNA/RNA attached to the column matrix. As Peptide1 is catalytically active towards the RNA, it will cleave the RNA and thereby release itself, to continue its migration through the column. The cleavage reaction of RNase A leaves the DNA/RNA hybrid of the Peptide1 beads with a 3'-phosphate, and the DNA/RNA coupled to the column with a 5'-hydroxyl. Polynucleotide kinase will catalyze the transformation of the 5'-hydroxyls and 3'-phosphate into 3'-hydroxyl and 5'-phosphate, respectively (Uhlenbeck, 1997, Chem. Rev., vol. 97, pp. 371–390). The DNA/RNA hybrids on the Peptide1 beads and the column are now ready for another ligation reaction, which will again immobilize the Peptide1 beads on the column matrix. It should be noted that the polynucleotide kinase is not required for a multiple turn-over selection, as each Peptide1 bead carries many DNA/RNA hybrids. Also, note that the RNA ligase will ligate both DNA and RNA.

The Peptide2 beads carry the mutant RNase, and will therefore spend more time immobilized on the column. Hence, after a number of turn-overs the Peptide1 beads will have separated from the Peptide2 beads as a result of their differential catalytic activity. The beads carrying the more active RNase A variant can therefore be collected first at the bottom of the column.

Selection stringency is controlled by the amount of Peptide and DNA/RNA hybrids immobilized on the beads, and by the concentration of RNA ligase, polynucleotide kinase and ATP in the buffer.

Using unnatural amino acids the catalytic machinery of RNase A may be examined, and potentially, new improved variants of RNase A evolved (Jackson et al., 1994, Science, vol. 266, pp. 243–247), using the substrate reloading selection outlined above. Alternatively, totally random peptide libraries may be searched for novel catalysts. The catalytically active peptides on the isolated beads can be identified by e.g. Edman degradation or mass spectrometry.

Example 6

Isolation of Active DNA Polymerase Variants Displayed on Phage, Using Restriction Enzymes for the Direct Reloading of Substrate This is an example of the selection protocol outlined in FIG. 2. A DNA primer is attached to a filamentous phage displaying a DNA polymerase (see FIG. 12). The DNA conjugated phages are passed through a column, coated with a DNA fragment complementary to the primer. The column is held under conditions of salt, pH and temperature where the two complementary strands transiently associates to form a DNA duplex. The duplex may fall apart soon after association; alternatively, the polymerase displayed on the corresponding phage may elongate the primer, resulting in a more stable complex. The latter event will efficiently immobilize the phage to the matrix. The column buffer also contains a restriction enzyme; the position of the recognition site for the restriction enzyme has been chosen so that cleavage by the restriction enzyme regenerates the original 3'-end of the primer attached to phage. Therefore, cleavage by the restriction enzyme results in substrate reloading.

Phage particles displaying the Klenow or Stoffel fragments of DNA polymerase I from *E. coli* are prepared according to the guidelines of (Jestin et al., 1999, Angew. Chem. Int. Ed., vol. 38, pp. 1124–1127) or (Pedersen et al., 1998, Proc. Natl. Acad. Sci. USA, vol. 95, pp. 10523–10528). The latter method involves the rescue of *E. coli* cells containing the phagemid encoding DNA polymerases with the Acid Helper phage.

A 10–80 nucleotides DNA oligo ("primer") with the sequence 5'-$N_x$-CCG-3' (in the case where EcoRI is employed in the selection protocol, see below), is attached to the phages as outlined in (Jestin et al., 1999, Angew. Chem. Int. Ed., vol. 38, pp. 1124–1127) or (Pedersen et al., 1998, Proc. Natl. Acad. Sci. USA, vol. 95, pp. 10523–10528), through the 5'-end.

A 20–80 nucleotides DNA oligo, ("template") with the sequence 3'-$N_y$-GGCTTAAG-$N_z$-5' (SEQ ID NO:12) (in the case where EcoRI is used in the selection protocol) is immobilized on a column matrix. For example, the oligo may be biotinylated at the 5'-end, and immobilized on streptavidin-coated, 4% agarose (Sigma), or immobilized by other standard methods. The length and composition of the complementary regions of "primer" and "template" oligos, are designed so as to obtain a transient (unstable) duplex of the primer and template under the conditions of the selection assay (see below).

Phages to which has been attached primer oligo (see above), are loaded on the DNA column in an appropriate buffer containing a restriction enzyme (EcoRI), dNTPs, 10–50 mM NaCl, pH 7.5–9, temperature 25–40° C. (see Jestin et al., 1999, Angew. Chem. Int. Ed., vol. 38, pp. 1124–1127). Phages will transiently become immobilized on the column through primer-template duplex formation; if the phage in question displays an active polymerase, the primer may become extended, resulting in a stabilization of the complex. If the primer is extended with more than 5 nucleotides, an EcoRI site will be created; EcoRI in the buffer will cleave at this site, which results in the regeneration of the original 3'-end of "primer" attached to phage, and destabilization of the duplex. The duplex may therefore fall apart, and the primer anneal to another template attached to the column matrix. This constitutes the reloading of substrate.

Phages displaying the more efficient polymerase will migrate slower through the column. Therefore, phages displaying the more efficient polymerase is collected in the later column fractions.

The protocol may be used for the isolation of polymerase variants that accept modified nucleotides as substrates, or accept templates carrying unnatural nucleotides, or modified nucleotides. Alternatively, the protocol may be performed using a phage displayed restriction enzyme, and polymerase as the reloading reagent in the buffer. This may allow the evolution of restriction enzymes with novel specificities.

Example 7

Isolation of Active DNA Polymerase Variants Displayed on Phage, Using Restriction Enzymes for the Direct Reloading of Substrate, in this Example Electrophoresis is Used as a Means to Isolate the More Efficient Polymerases.

In this example a DNA primer is attached to a filamentous phage displaying a DNA polymerase. The DNA conjugated phages are mixed with long single stranded DNA molecules, containing a region that is complementary to the primer, and loaded on an electrophoresis gel. The length and composition of the complementary regions are designed so that the two complementary strands form transient DNA duplex complexes under the conditions of eletrophoresis (see FIG. 13). The duplex may fall apart soon after association; alternatively, the polymerase displayed on the corresponding phage may elongate the primer, resulting in a more stable complex. The latter event will efficiently attach the DNA fragment to the phage, and thereby influence its migration rate in the electrical field. The eletrophoresis buffer also contains a restriction enzyme in high concentration; the position of the recognition site for the restriction enzyme has been chosen so that cleavage by the restriction enzyme regenerates the original 3'-end of the primer attached to phage, and destabilizes the complex. Therefore, cleavage by the restriction enzyme results in substrate reloading.

Phage particles displaying the Klenow or Stoffel fragments of DNA polymerase I from *E. coli* are prepared according to the guidelines of (Jestin et al., 1999, Angew. Chem. Int. Ed., vol. 38, pp. 1124–1127) or (Pedersen et al., 1998, Proc. Natl. Acad. Sci. USA, vol. 95, pp. 10523–10528). The latter method involves the rescue of *E. coli* cells containing the phagemid encoding DNA polymerases with the Acid Helper phage.

A 10–80 nucleotides DNA oligo ("primer") with the sequence 5'-$N_x$-CCG-3' (in the case where EcoRI is employed in the selection protocol, see below), is attached to the phages through the 5'-end, as outlined in (Jestin et al., 1999, Angew. Chem. Int. Ed., vol. 38, pp. 1124–1127) or (Pedersen et al., 1998, Proc. Natl. Acad. Sci. USA, vol. 95, pp. 10523–10528).

A single stranded DNA of 100–1000 nucleotides, with the sequence 3'-Ny-GGCTTAAG-Nx-5' (SEQ ID NO:12) (in the case where the restriction enzyme is EcoRI), is prepared by standard methods. For example, a PCR reaction may be performed with the primers "fwd" (5'-biotin-N-CCGAATTC-N-3') (SEQ ID NO:13) and "bck", on a template with annealing sites for the two primers spaced 100–1000 base pairs apart. The resulting PCR product is immobilized on streptavidin beads, and the non-biotinylated strand eluted at high pH. The eluted strand has the sequence 3'-N-GGCTTAAG-N-5', (SEQ ID NO:12) and length 100–1000 nucleotides.

The length and composition of the complementary regions of "primer" and "template" oligos ($N_x$ and $N_y$), are designed so as to obtain a transient (unstable) duplex of the primer and template under the conditions of the selection assay (see below).

Phages to which has been attached primer oligo (see above), are loaded on the electrophoresis gel in an appropriate buffer containing a restriction enzyme (EcoRI), dNTPs, 10–50 mM NaCl, pH 6–9, temperature 25–40° C.

(see Jestin et al., 1999, Angew. Chem. Int. Ed., vol. 38, pp. 1124–1127), and the 100–1000 nucleotides single stranded DNA described above. Concentrations of the 100–1000 nucleotides DNA molecule may be 0.1–10 $\mu$M in the gel, 0.01–1 $\mu$M in the buffer. Phages will transiently form the primer-template duplex; if the phage in question displays an active polymerase, the primer may become extended, resulting in a stabilization of the complex. If the primer is extended with more than 5 nucleotides, an EcoRI site is created; EcoRI in the buffer will cleave at this site, which results in the regeneration of the original 3'-end of "primer" attached to phage, and destabilization of the duplex. The duplex may therefore fall apart, and the primer anneal to another template. This constitutes the reloading of substrate.

Phages displaying an efficient polymerase will more efficiently form the stable duplex, and therefore (because of the added charge and mass of the DNA fragment) migrate differently from phages displaying inefficient polymerase. The principle is tested with a small model library of polymerase variants.

The protocol may be used for the isolation of polymerase variants that accept modified nucleotides as substrates, or accept templates carrying unnatural nucleotides, or modified nucleotides. In the inverse set-up, the protocol may be performed using phage displayed restriction enzymes and polymerase as the reloading reagent in the buffer. This may allow the evolution of restriction enzymes with novel specificities.

Example 8

Optimization of a deoxy-ribozyme with Ligase Activity

In this example, a deoxy-ribonucleotide-based catalyst with RNA-ligation activity is sought optimized through substrate reloading by RNase and polynucleotide kinase.

A model library consisting of a few variants of the deoxy-ribozyme is prepared and folded by standard methods. Then, a DNA/RNA hybrid consisting of 20–40 deoxy-ribonucleotides at the 5'-end and one ribonucleotide at the 3'-end, is annealed through the DNA portion to the deoxy-ribozyme (the DNA/RNA hybrid is designed with a complementary sequence to one of the amplification-primer annealing sites on the deoxy-ribozyme; the formation of the duplex should therefore not interfere with the activity of the deoxy-ribozyme) see FIG. 14.

The deoxy-ribozyme-oligonucleotide complex is loaded on a column, to which has been attached a DNA/RNA hybrid of 20–40 nucleotides, of which the 5'-nucleotide is a ribonucleotide, and the rest are deoxy-ribonucleotides. The hybrid is attached to the column through the 3'-end. The column buffer contains RNase, polynucleotide kinase, ATP, buffer of pH 6–9, MgCl$_2$, plus other components necessary for the activity of the ligase, RNase and polynucleotide kinase, as well as for efficient annealing. The temperature is held between 20–40° C., and the buffer flow below 0.5 mL/min.

Active ligases will become immobilized on the column by ligation of the 3'- and 5'-ends of the DNA/RNA hybrids. RNase will cleave the formed di-ribonucleotide; this creates 3'-phophates and 5'-hydroxyls. Polynucleotide kinase will remove the 3'-phosphates and introduce 5'-phosphates. This constitutes the substrate reloading step, and the DNA/RNA hybrids can now be ligated together again by the deoxy-ribozyme. The more efficient ligases in the pool can be collected from the later fractions. This type of selections should make it possible to improve the activity of ribozymes, which are generally rather poor, typically on the order of 1 min$^{-1}$.

Example 9

Pre-Enrichment of Phages Displaying His-Tagged Proteins

Certain proteins are difficult to display on filamentous phage. In particular, large proteins or proteins which have a toxic or growth inhibiting effect on *E. coli* often have low display efficiency, i.e. the majority of phage particles produced carry no pIII-fusion on the surface. Display efficiencies as low as one out of a thousand phages displaying the fusion protein have been reported (Jestin et al., 1999, Angew. Chemi. Int. Ed., vol. 38, pp. 1124–1127; Demartis et al., 1999, JMB, vol. 286, pp. 617–633). In such cases, a high non-specific background is expected, because of the large excess of phage particles carrying the DNA encoding the pIII fusion, but not displaying the fusion on the surface. To circumvent this potential problem, we inserted a histidine tag between the pIII coat protein and the enzyme, allowing the purification of phages displaying His-tagged protein by Ni-NTA column chromatography.

Other tags that could have been used in a similar manner as described below for the Histidine tag include the intein-chitin binding domain fusion (Chong et al., 1997, Gene, vol. 192, pp 271–281), FLAG peptide (Slootstra et al., 1997, Molecular Diversity, vol. 2, pp. 156–164), and the maltose binding protein (Pryor and Leiting, 1997, Protein expression and Purification, vol. 10, pp. 309–319).

Ni-NTA Column Purification of Phages Displaying the Lipase-His6-pIII or Cellulase-His6-pIII Fusion Protein.

A Ni-NTA spin column (Qiagen Spin Kit) was equilibrated with 600 $\mu$L "50 mM sodium-phosphate buffer pH 8, 300 mM NaCl, 1 mM Imidazole, 0.05% BSA" (centrifuged 2 minutes at 700 G). To 400 $\mu$l phage preparation (approximately 10$^{12}$ phage particles) was added 100 $\mu$L "250 mM sodium-phosphate buffer pH 8, 1.5 M NaCl, 0.25% BSA" and 4 $\mu$L 100 mM Imidazole, the solution loaded onto the pre-equilibrated column, and centrifuged for 4 minutes at 200 G. The column was washed twice with 600 $\mu$L "50 mM sodium-phosphate buffer pH 8, 300 mM NaCl, 20 mM Imidazole, 0.05% BSA" (centrifugation 200 G for 4 minutes and 700 G for 2 minutes, respectively). Then the phages were eluted with 3×333 $\mu$L "50 mM sodium-phosphate buffer pH 8, 300 mM NaCl, 250 mM Imidazole, 0.05% BSA" (700 G, 2 minutes), and the 999 AL eluate PEG precipitated and resuspended in 400 $\mu$L "50 mM sodium-phosphate buffer pH 8, 300 mM NaCl, 1 mM Imidazole, 0.05% BSA". The solution was loaded on a fresh spin column, and the procedure repeated, except that the final PEG precipitate was dissolved in 50 $\mu$L TE buffer pH 8. This procedure enriches approximately 500 fold for phage displaying His-tagged protein.

What is claimed is:

1. A method for identifying a catalyst of interest from a library comprising at least two different potential catalysts, said method comprising:
   a) providing a library of units comprising potential catalysts, at least two different potential catalysts presented in the library as components of different individual units, each unit having the structure potential catalyst-substrate, indicating that at least one potential catalyst molecule is attached to at least one substrate molecule, wherein said potential catalyst is attached to said at least one substrate in a manner that allows a potential catalytic reaction to occur between said potential catalyst and said at least one substrate;
   b) providing conditions suitable for said potential catalyst, to catalyze the reaction of said at least one substrate to form one or more products, wherein at least one product of said catalytic reaction remains attached to said catalyst;
   c) providing at least one reagent or condition which converts said at least one attached product to at least one substrate so as to regenerate at least one catalyst-substrate unit;
   d) repeating said b) and c) at least once; and
   e) identifying at least one catalyst, with the desired catalytic activity.

2. The method of claim 1, wherein said potential catalyst is biologically amplifiable.

3. The method of claim 1, wherein said unit is biologically amplifiable and said potential catalyst and said at least one substrate attached to said potential catalyst are attached on the surface of said biologically amplifiable unit.

4. The method of claim 1, wherein said potential catalyst is attached to said at least one substrate by a flexible linker.

5. The method of claim 1, wherein said potential catalyst is attached to said at least one substrate by a carrier system.

6. The method of claim 1, wherein said potential catalyst is attached to said at least one substrate by a flexible linker and a carrier system.

7. The method of claim 5, wherein said carrier system is a bead particle.

8. The method of claim 1, wherein said potential catalysts are peptides or polypeptides.

9. The method of claim 8, wherein said peptides or polypeptides are enzymes.

10. The method of claim 9, wherein said peptides or polypeptides are recombinantly produced.

11. The method of claim 9, wherein said peptides or polypeptides include shuffled peptides or polypeptides.

12. The method of claim 9, wherein said peptides or polypeptides include doped polypeptides.

13. The method of claim 1, wherein the potential catalyst and the at least one substrate are different chemical substances.

14. The method of claim 1, wherein said potential catalysts are peptides or polypeptides, and in synthesizing said potential catalysts, some of the peptides or polypeptides obtained are shorter than intended, and said method entails prior to said a), removing at least some of the shorter than intended peptides or polypeptides to obtain a library which is enriched for full-length peptides or polypeptides.

15. The method of claim 1, which comprises immobilizing said product molecule.

16. The method of claim 15, which comprises immobilizing said product molecule on an affinity column.

17. The method of claim 15, which comprises immobilizing said product molecule on a bead.

18. The method of claim 15, immobilizing said product on a microchip.

19. The method of claim 1, wherein said actual catalyst and the at least one substrate are bound to a matrix, and wherein said catalyst is released from said matrix when said at least one substrate is converted to said at least one product by said actual catalyst.

20. The method of claim 2, wherein said identifying is performed by providing a column having at least one receptor that is able to bind said at least one product, and then identifying the actual catalyst bound through said product to said receptor.

21. The method of claim 1 wherein the attachment of potential catalyst to substrate within an individual unit is covalent.

22. The method of claim 1 where the substrate is regenerated in step (c) using a reaction pathway different from the pathway which generated the product in step (b).

23. The method of claim 1 where the substrate is regenerated in step (c) using a reaction catalyzed by a catalyst which is not a member of any of said units.

24. The method of claim 1 where the substrate is regenerated in step (c) by reacting the product of step (b) with a reagent, such reaction resulting in production of said substrate, said reaction being energetically favored.

25. The method of claim 1 wherein the regeneration step is energetically unfavorable, but is coupled to an energetically favorable reaction.

26. The method of claim 25 in which the energetically favorable reaction is hydrolysis of ATP.

27. The method of claim 1 in which the library comprises at least one unit comprising a known catalyst.

* * * * *

SEQUENCE LISTING

<160> NUMBER OF SEQ ID NOS: 13

<210> SEQ ID NO 1
<211> LENGTH: 46
<212> TYPE: PRT
<213> ORGANISM: Artificial Sequence
<220> FEATURE:
<223> OTHER INFORMATION: Synthetic

<400> SEQUENCE: 1

Cys Gly Gly Ser Gly Gly Ser Gly Gly Ser Gly Gly Ser Ala Gln Leu
1               5                   10                  15

Lys Lys Lys Leu Gln Ala Leu Lys Lys Lys Asn Ala Gln Leu Lys Trp
            20                  25                  30

Lys Leu Gln Ala Leu Lys Lys Lys Leu Ala Gln Gly Gly Cys
        35                  40                  45

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
acaactttca acggcgccag tttcagcgg                                          29

<210> SEQ ID NO 3
<211> LENGTH: 39
<212> TYPE: PRT
<213> ORGANISM: Artificial Sequence
<220> FEATURE:
<223> OTHER INFORMATION: Synthetic

<400> SEQUENCE: 3

Gly Ala Ala Gln Leu Glu Lys Glu Leu Gln Ala Leu Glu Lys Glu Asn
1               5                   10                  15

Ala Gln Leu Glu Trp Glu Leu Gln Ala Leu Glu Lys Glu Leu Ala Gln
            20                  25                  30

Gly Gly Cys Pro Ala Gly Ala
        35

<210> SEQ ID NO 4
<211> LENGTH: 35
<212> TYPE: DNA
<213> ORGANISM: Artificial Sequence
<220> FEATURE:
<223> OTHER INFORMATION: Primer

<400> SEQUENCE: 4
actacaaatt ggcgccgctc agctcgaaaa agagc                                   35

<210> SEQ ID NO 5
<211> LENGTH: 47
<212> TYPE: DNA
<213> ORGANISM: Artificial Sequence
<220> FEATURE:
<223> OTHER INFORMATION: Primer

<400> SEQUENCE: 5
aattataggc gccagccggg caaccgccct gagccagttc cttttcc                      47

```
<210> SEQ ID NO 6
<211> LENGTH: 42
<212> TYPE: DNA
<213> ORGANISM: Artificial Sequence
<220> FEATURE:
<223> OTHER INFORMATION: Primer

<400> SEQUENCE: 6
cgcgaattgg cccagccggc catggccgca acttcaacta aa                         42

<210> SEQ ID NO 7
<211> LENGTH: 37
<212> TYPE: DNA
<213> ORGANISM: Artificial Sequence
<220> FEATURE:
<223> OTHER INFORMATION: Primer

<400> SEQUENCE: 7
gcgaattggt gcggccgctt gacctgaatc agcgttg                              37

<210> SEQ ID NO 8
<211> LENGTH: 39
<212> TYPE: PRT
<213> ORGANISM: Artificial Sequence
<220> FEATURE:
<223> OTHER INFORMATION: Synthetic

<400> SEQUENCE: 8

Gly Ala Ala Gln Leu Glu Lys Glu Leu Gln Ala Leu Glu Lys Glu Asn
 1               5                  10                  15

Ala Gln Leu Glu Trp Glu Leu Gln Ala Leu Glu Lys Glu Leu Ala Gln
            20                  25                  30

Gly Gly Cys Pro Ala Gly Ala
        35

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gccgaagcgc aatgaagggc                                                 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gcccttcatt gcgcttcggc                                                 20

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
gccgaagcgc aatgaagggc aacccg                                          26
```

-continued

```
<210> SEQ ID NO 12
<211> LENGTH: 10
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(10)
<223> OTHER INFORMATION: n = A,T,C or G

<400> SEQUENCE: 12 nggcttaagn                                                                    10

<210> SEQ ID NO 13
<211> LENGTH: 10
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(10)
<223> OTHER INFORMATION: n = A,T,C or G

<400> SEQUENCE: 13 nccgaattcn                                                                10
```